United States Patent
Mische et al.

(10) Patent No.: US 10,371,636 B2
(45) Date of Patent: Aug. 6, 2019

(54) MODULAR TESTING DEVICE FOR ANALYZING BIOLOGICAL SAMPLES

(71) Applicant: Agdia Inc., Elkhart, IN (US)

(72) Inventors: Hans Mische, Grey Eagle, MN (US); Grant Pexsa, Alexandria, MN (US); Mark Baumgartner, Alexandria, MN (US); Cory Hodgson, Alexandria, MN (US); Andrew Bristow, Alexandria, MN (US); John Steckelberg, Sauk Centre, MN (US); Jared Patterson, Alexandria, MN (US)

(73) Assignee: AGDIA INC., Elkart, IN (US)

(*) Notice: Subject to any disclaimer, the term of this patent is extended or adjusted under 35 U.S.C. 154(b) by 0 days.

(21) Appl. No.: 15/561,901

(22) PCT Filed: Mar. 25, 2016

(86) PCT No.: PCT/US2016/024260
§ 371 (c)(1),
(2) Date: Sep. 26, 2017

(87) PCT Pub. No.: WO2016/154555
PCT Pub. Date: Sep. 29, 2016

(65) Prior Publication Data
US 2018/0202932 A1    Jul. 19, 2018

Related U.S. Application Data

(60) Provisional application No. 62/138,157, filed on Mar. 25, 2015.

(51) Int. Cl.
*G01N 21/64* (2006.01)
*G01N 21/25* (2006.01)
(Continued)

(52) U.S. Cl.
CPC .......... *G01N 21/6428* (2013.01); *B01L 3/527* (2013.01); *B01L 7/52* (2013.01);
(Continued)

(58) Field of Classification Search
CPC ........ G01N 21/65; G01N 21/64; G01N 33/50; G01N 21/25; G01N 21/27; B01L 7/00; B01L 3/00
See application file for complete search history.

(56) References Cited

U.S. PATENT DOCUMENTS

| 3,810,367 A | 5/1974 | Peterson |
| 8,615,374 B1 | 12/2013 | Discenzo |

(Continued)

FOREIGN PATENT DOCUMENTS

| WO | 2012149555 A1 | 11/2012 |
| WO | 2016154555 A1 | 9/2016 |

OTHER PUBLICATIONS

U.S. Patent and Trademark Office; PCT International Search Report, Issued in Connection to PCT/US16/24260; dated Jun. 24, 2016; 2 pages; U.S.

(Continued)

*Primary Examiner* — Abdullahi Nur
(74) *Attorney, Agent, or Firm* — Kilpatrick Townsend & Stockton LLP

(57) ABSTRACT

A modular testing device includes a base unit and an expansion unit that communicates with the base unit. The expansion unit includes a housing, a receptacle in which a sample holder containing a biological sample and reagent mixture can be placed, and an optical assembly positioned in the housing. The optical assembly is configured to amplify and detect a signal from the biological sample and reagent mixture. Data that is collected in the optical assembly is communicated to the base unit.

18 Claims, 17 Drawing Sheets

(51) Int. Cl.
*G01N 33/50* (2006.01)
*B01L 3/00* (2006.01)
*B01L 7/00* (2006.01)

(52) U.S. Cl.
CPC ......... *G01N 21/253* (2013.01); *G01N 21/645* (2013.01); *G01N 33/50* (2013.01); *B01L 2300/0609* (2013.01); *B01L 2300/0893* (2013.01); *G01N 2021/6439* (2013.01); *G01N 2021/6482* (2013.01); *G01N 2201/024* (2013.01); *G01N 2201/062* (2013.01); *G01N 2201/0691* (2013.01)

(56) References Cited

U.S. PATENT DOCUMENTS

| | | |
|---|---|---|
| 2006/0066850 A1 | 3/2006 | Kimura |
| 2013/0011912 A1 | 1/2013 | Battrell et al. |
| 2013/0210127 A1 | 8/2013 | Williams et al. |
| 2014/0045250 A1 | 2/2014 | Kreifels et al. |
| 2016/0245690 A1* | 8/2016 | Nammoku ............ G01N 21/51 |
| 2017/0113221 A1* | 4/2017 | Hoffman .......... G01N 35/00069 |

OTHER PUBLICATIONS

U.S. Patent and Trademark Office; PCT Written Opinion of the International Searching Authority, Issued in Connection to PCT/US16/24260; dated Jun. 24, 2016; 8 pages; U.S.
EP16769783.8 , "Extended European Search Report", dated Sep. 17, 2018, 8 pages.

\* cited by examiner

MODULAR TESTING DEVICE FOR ANALYZING BIOLOGICAL SAMPLES

CROSS-REFERENCE TO RELATED APPLICATION(S)

This application is the 35 U.S.C. § 371 national application of International Patent Application No. PCT/US2016/024260, filed Mar. 25, 2016, which designated the United States and claimed priority to provisional U.S. Provisional Application No. 62/138,157, filed on Mar. 25, 2015, and entitled "Modular Testing Device for Analyzing Biological Samples," the disclosure of which are incorporated by reference in their entirety.

BACKGROUND

The present invention relates to devices that are capable of analyzing biological samples, and in particular, to a modular testing device for analyzing biological samples.

Biological samples are typically tested in laboratories after the biological samples are collected in the field. A number of steps are taken to prepare the sample after it has been collected, including mixing the sample with reaction buffers, dyes, and any other chemical solutions needed to prepare the sample for testing. During or after sample preparation, testing equipment also needs to be prepared. This can include warming up the equipment, calibrating the equipment for the specific tests to be run, and running through any other initial procedures required for the specific testing equipment being used. Once the sample and the equipment are prepared, the prepared sample can be placed in the equipment for testing.

The typical process for testing biological samples described above has significant disadvantages. One disadvantage is that biological samples need to be collected in the field, brought into the laboratory, and then tested. This can present the following issues. One, the biological sample can be contaminated between the time when it was collected and time that it is to be tested. Two, it can be discovered that not enough biological sample was collected in the field, preventing the testing from being complete. Three, it can be later discovered that the biological samples that were taken are otherwise unsuitable for testing. When a biological sample is unsuitable for testing for any of the above reasons, an additional biological sample will need to be collected in order to complete the testing. This requires additional time, money, and other resources to complete.

To eliminate the problems discussed above, portable testing devices are available for analyzing biological samples in the field. One such device is disclosed in PCT Application No. PCT/US14/59487, filed on Oct. 7, 2014, and entitled "Portable Testing Device For Analyzing Biological Samples," the disclosure of which is incorporated by reference in its entirety. In order to be portable, the testing devices need to be small enough so that they can be easily transported. This limitation on the size of portable testing devices limits the number of biological samples that can be tested at one time.

SUMMARY

A modular testing device includes a base unit and an expansion unit that communicates with the base unit. The expansion unit includes a housing, a receptacle in which a sample holder containing a biological sample and reagent mixture can be placed, and an optical assembly positioned in the housing. The optical assembly is configured to amplify and detect a signal from the biological sample and reagent mixture. Data that is collected in the optical assembly is communicated to the base unit.

A modular testing device includes a base unit and an expansion unit that communicates with the base unit. The base unit includes a housing with an integrated touchscreen display, a receptacle in which a sample holder containing a biological sample and reagent mixture can be placed, and an optical assembly positioned in the housing. The optical assembly is configured to amplify and detect a signal from the biological sample and reagent mixture. The expansion unit includes a housing, a receptacle in which a sample holder containing a biological sample and reagent mixture can be placed, and an optical assembly positioned in the housing. The optical assembly is configured to amplify and detect a signal from the biological sample and reagent mixture.

A method of analyzing a biological sample and reagent mixture in a modular testing device includes preparing a biological sample and reagent mixture for testing and placing the biological sample and reagent mixture in a sample holder. The sample holder is placed in a receptacle in an expansion unit. An excitation and detection test sequence is begun to analyze the biological sample and reagent mixture in the expansion unit. Data is collected from the excitation and detection test sequence in the expansion unit. The data is communicated from the expansion unit to a base unit.

DETAILED DESCRIPTION

In general, the present disclosure relates to modular testing devices for analyzing biological samples. In the embodiments described below, the modular testing device is capable of testing biological samples with an isothermal amplification process, such as NEAR chemistry, LAMP chemistry, RPA chemistry, or NASBA chemistry. This eliminates the need for thermocycling as a means to amplify nucleic acid products for endpoint detection.

Figure 1A:
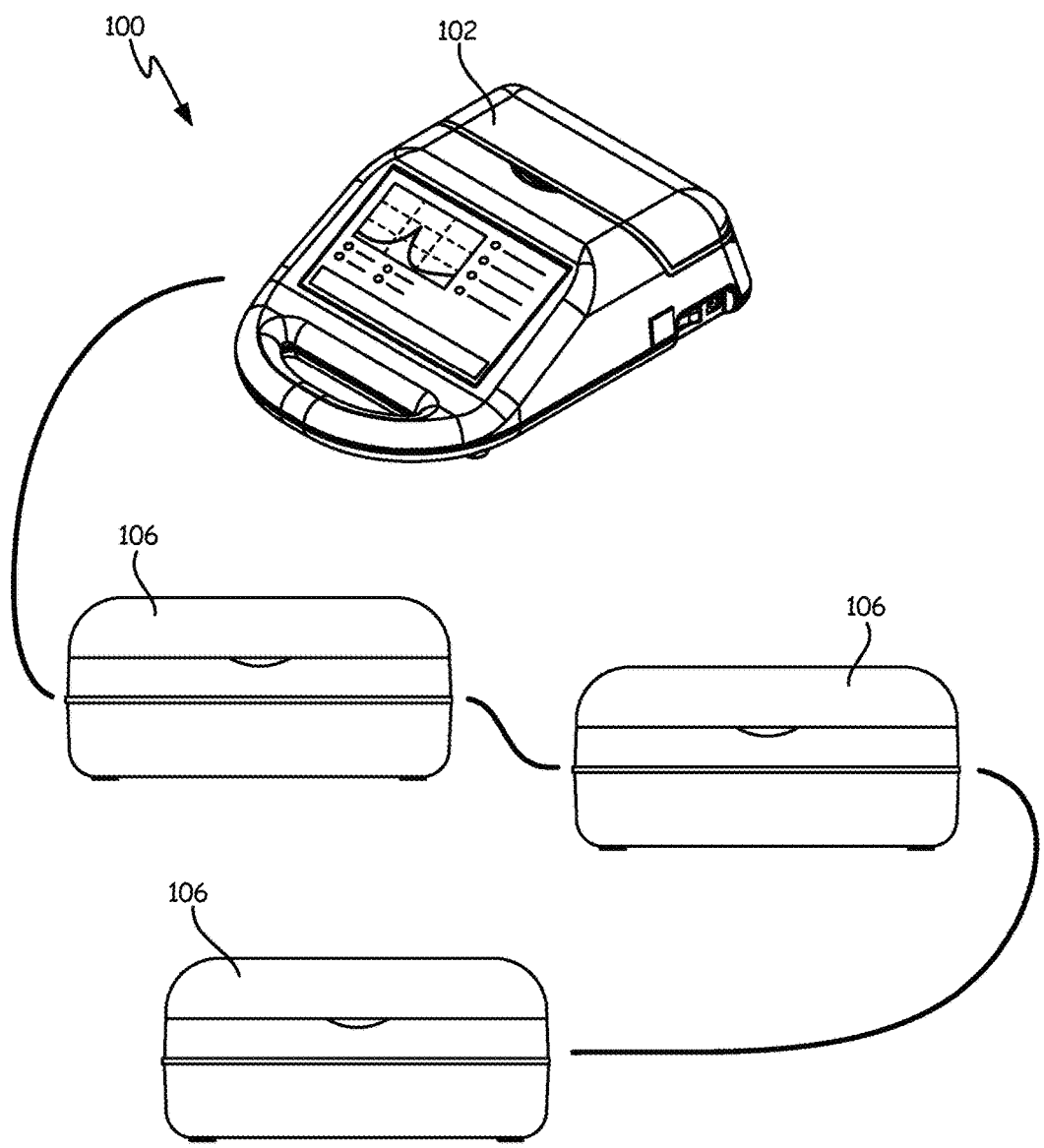
FIG. 1A is a diagram of a first embodiment of a modular testing device including a base unit and an expansion unit.
Figure 1B:
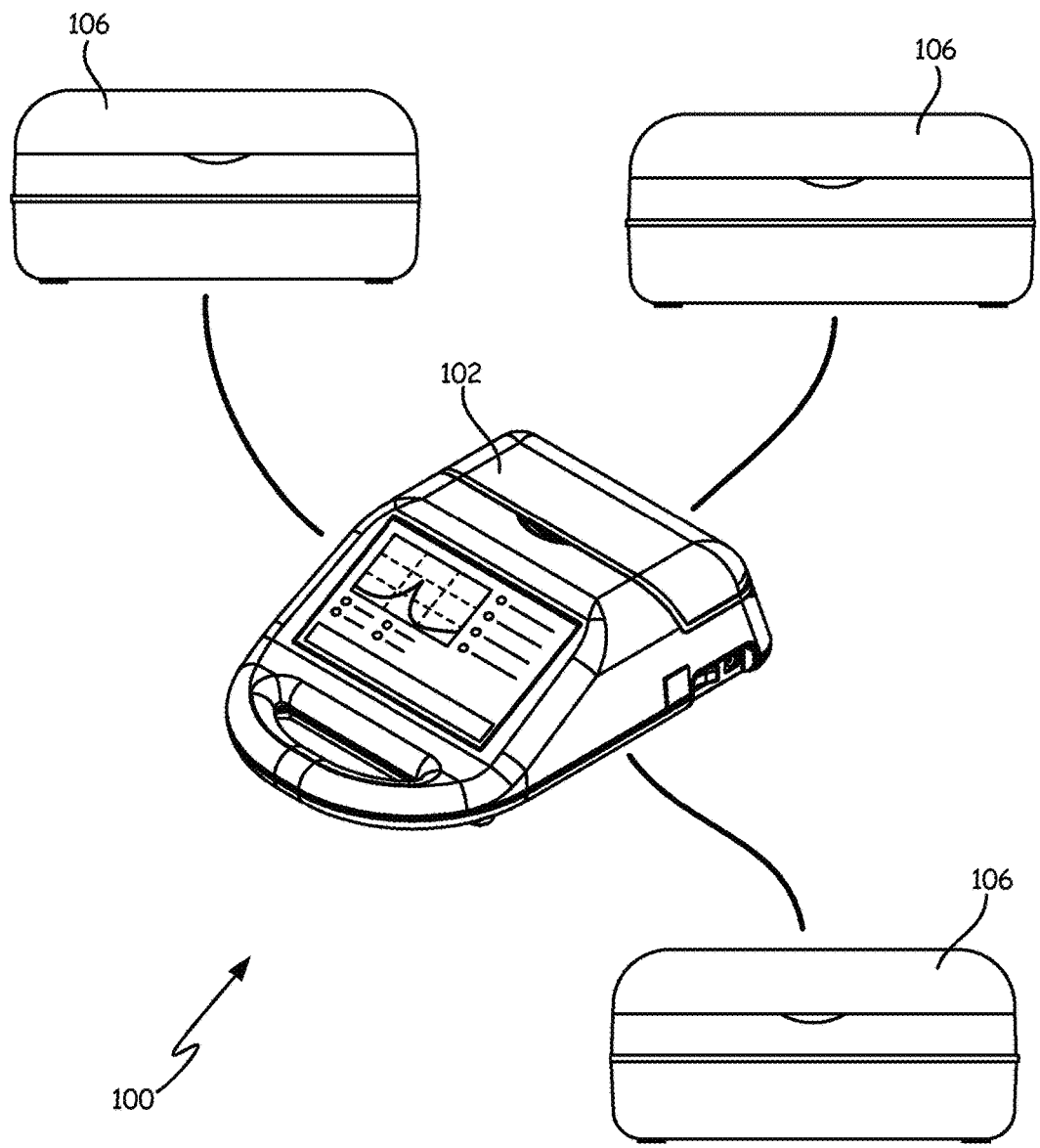
FIG. 1B is a diagram of a second embodiment of a modular testing device including a base unit and an expansion unit.
Figure 1C:
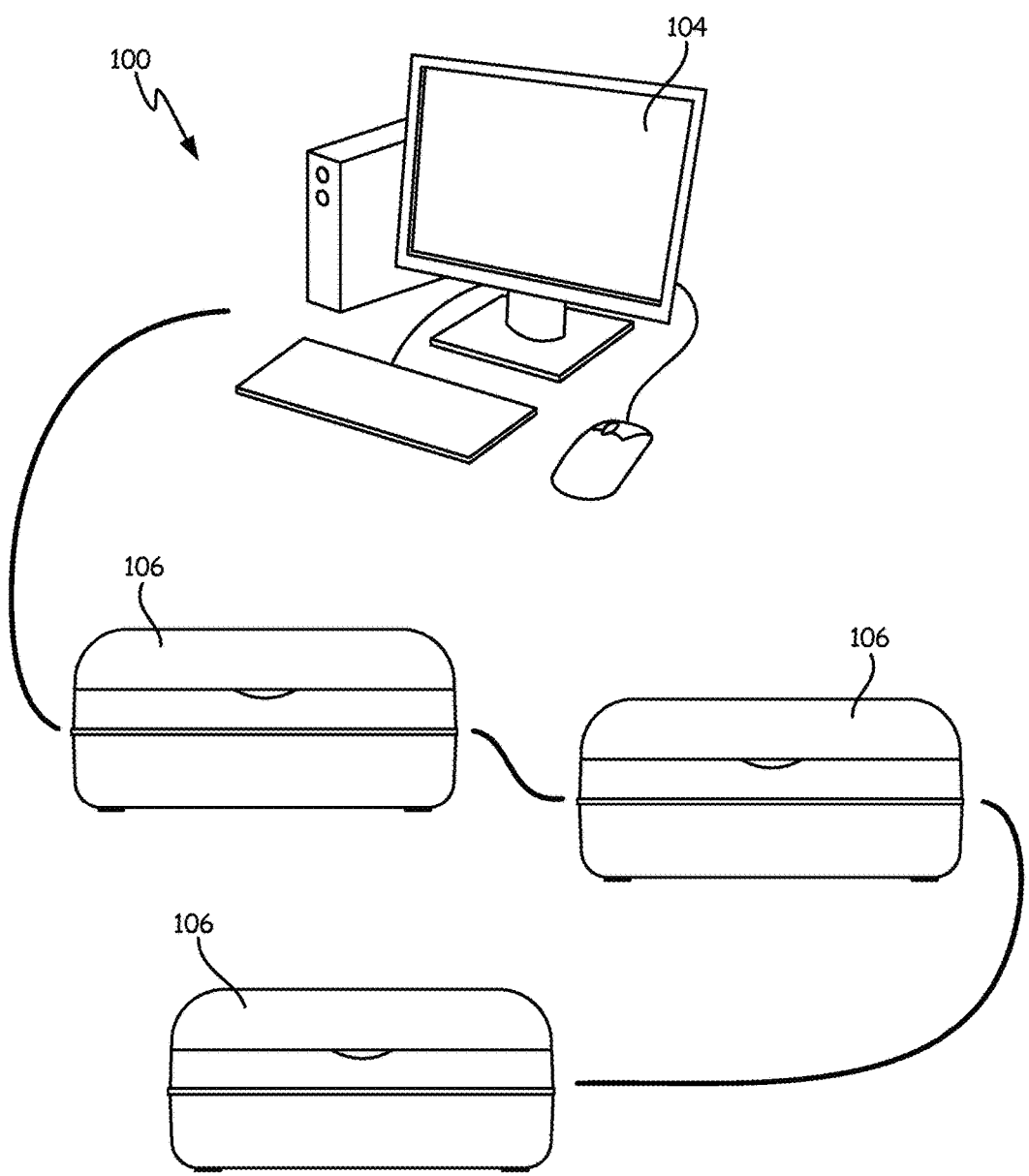
FIG. 1C is a diagram of a third embodiment of a modular testing device including a base unit and an expansion unit.

FIG. 1A is a diagram of modular testing device 100 including base unit 102 and expansion units 106. FIG. 1B is a diagram of modular testing device 100 including base unit 102 and expansion units 106. FIG. 1C is a diagram of modular testing device 100 including base unit 104 and expansion units 106.

Modular testing device 100 includes a base unit, including either base unit 102 or base unit 104, and one or more expansion units 106. In FIGS. 1A-1B, modular testing device 100 is shown with base unit 102. Base unit 102 can be used to analyze biological samples that have been mixed with a reaction mixture (also referred to as a biological sample and reagent mixture). Base unit 102 includes an optical assembly to amplify, excite, and detect a biological sample that is placed in base unit 102 for testing. Base unit 102 further includes a power supply to power base unit 102, an electronic assembly including components that are capable of running test protocol, and a screen that a user can interface with to select parameters for the test protocol and which can display data as it is collected. In FIG. 1C, modular testing device 100 is shown with base unit 104. Base unit 104 is a desktop computer in the embodiment shown, but can be a laptop computer, tablet computer, a mobile phone, a smart watch, an embedded PC, or any other suitable computer in alternate embodiments. Base unit 104 includes a power supply to power base unit 104, an electronic assembly including components that are capable of running test protocols, a machine readable code reader, and a screen that a user can interface with to select parameters for the test protocol and which can display data as it is collected.

In the embodiment shown in FIGS. 1A-1C, three expansion units 106 are shown. In alternative embodiments, any number of expansion units 106 can be used. Each expansion unit 106 includes an optical assembly to amplify, excite, and detect a biological sample that is placed in base unit 102 for testing. In the embodiment shown in FIGS. 1A-1C, each expansion unit 106 further includes a power supply to power expansion unit 106. In an alternate embodiment, expansion unit 106 does not have a power supply but is instead powered by a base unit. Each expansion unit 106 further includes an electronic assembly including components that are capable of communicating data to the base unit. Each expansion unit 106 interfaces with and is controlled by the base unit, either base unit 102 or base unit 104. The base unit communicates with expansion units 106 to indicate what testing is to be run in expansion units 106 and when testing is to be initiated. Expansion units 106 can be connected to the base unit with a hard wire connection or expansion units 106 can be connected to the base unit with a wireless connection. Testing can be completed in each expansion unit 106 using the optical assembly and data collected during the testing is communicated to the base unit. The data can be processed in expansion units 106 before it is communicated to the base unit or it can be communicated to the base unit before being processed. Either way, the data can also be processed in the base unit.

In the embodiments shown in FIGS. 1A and 1C, a first expansion unit 106 is connected to the base unit, a second expansion unit 106 is connected to the first expansion unit 106, and a third expansion unit 106 is connected to the second expansion unit 106. In the embodiment shown in FIG. 1B, expansion units 106 are each connected to the base unit. Further, in alternate embodiments, expansion units 106 can be connected to one another or the base units can be connected to one another. In one embodiment, for example, a first base unit 102 could be connected to a second base unit 102. The first base unit 102 could communicate to the second base unit 102 what testing to run and when to initiate testing. The first base unit 102 and the second base unit 102 could conduct testing at the same time or at different times. In each of FIGS. 1A-1C, expansion units 106 and the base units can be connected using a hardwire connection or a wireless connection.

Expansion units 106 can conduct testing of a biological sample at the same time or at different times. For example, each expansion unit 106 can be loaded with a biological sample. The base unit can then indicate to each expansion unit 106 that testing is to begin at the same time. Alternately, a first expansion unit 106 can be loaded with a biological sample and the base unit can indicate that the first expansion unit 106 is to begin testing. A second expansion unit 106 can then be loaded with a biological sample and the base unit can then indicate that the second expansion unit 106 is to begin testing.

Expansion units 106 can test a biological sample using turbidity, fluorescence, chemiluminescence, thermoluminescence, photometric, absorbance, or radiometric means. Expansion units 106 can also run different analytical methods, for example immunoassay, DNA amplification, mass spectrometry, or high-performance liquid chromatography. A single base unit can control expansion units 106 that are using different tests and running different analytical methods.

Modular testing device 100 is advantageous, as it allows a user to customize its modular testing device 100 for different applications. Expansion units 106 can be used with base unit 102 when a user wants to conduct testing in the field. Expansion units 106 can also then be used with base unit 104 when a user is conducting testing in a laboratory setting. Expansion units 106 also allow a user to customize how many tests are run during a testing protocol. Modular testing device 100 can also include a rack that is capable of holding expansion units 106. The rack can be designed to fit over the base unit so that expansion units 106 can be positioned on the rack over the base unit.

Figure 2A:
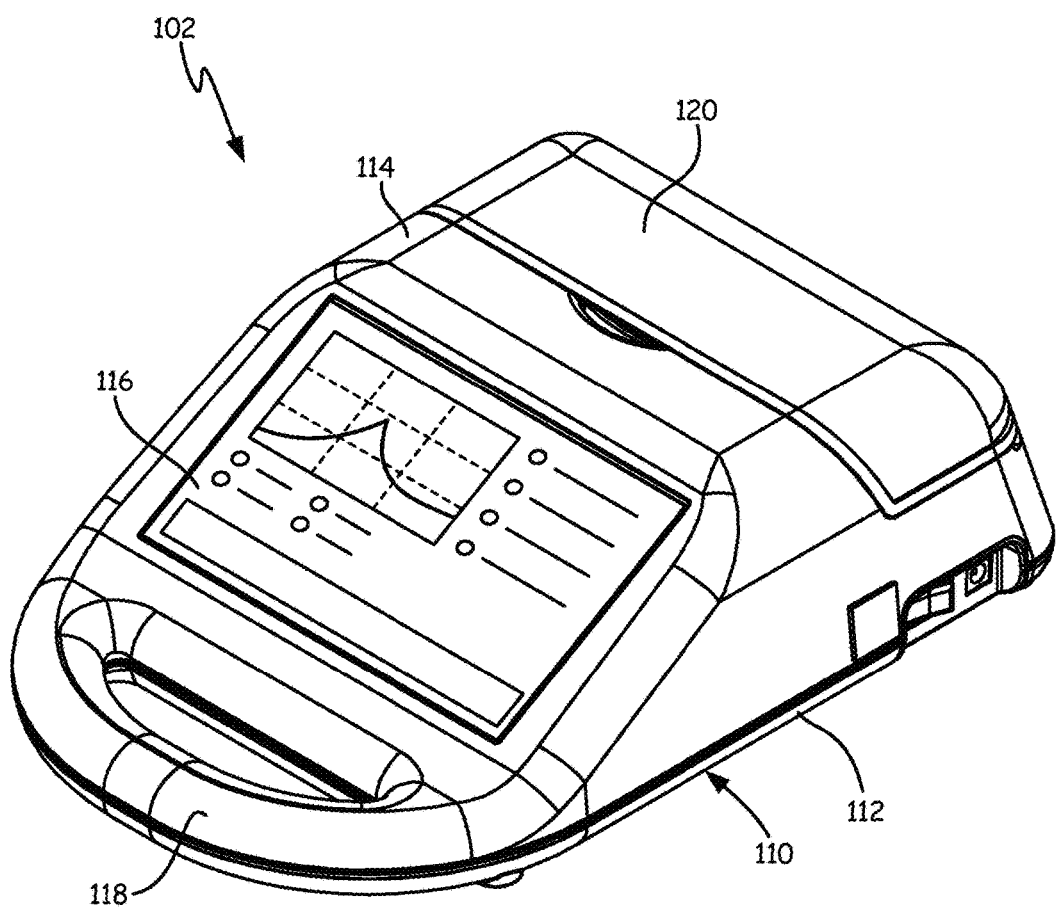
FIG. 2A is a perspective view of a base unit.
Figure 2B:
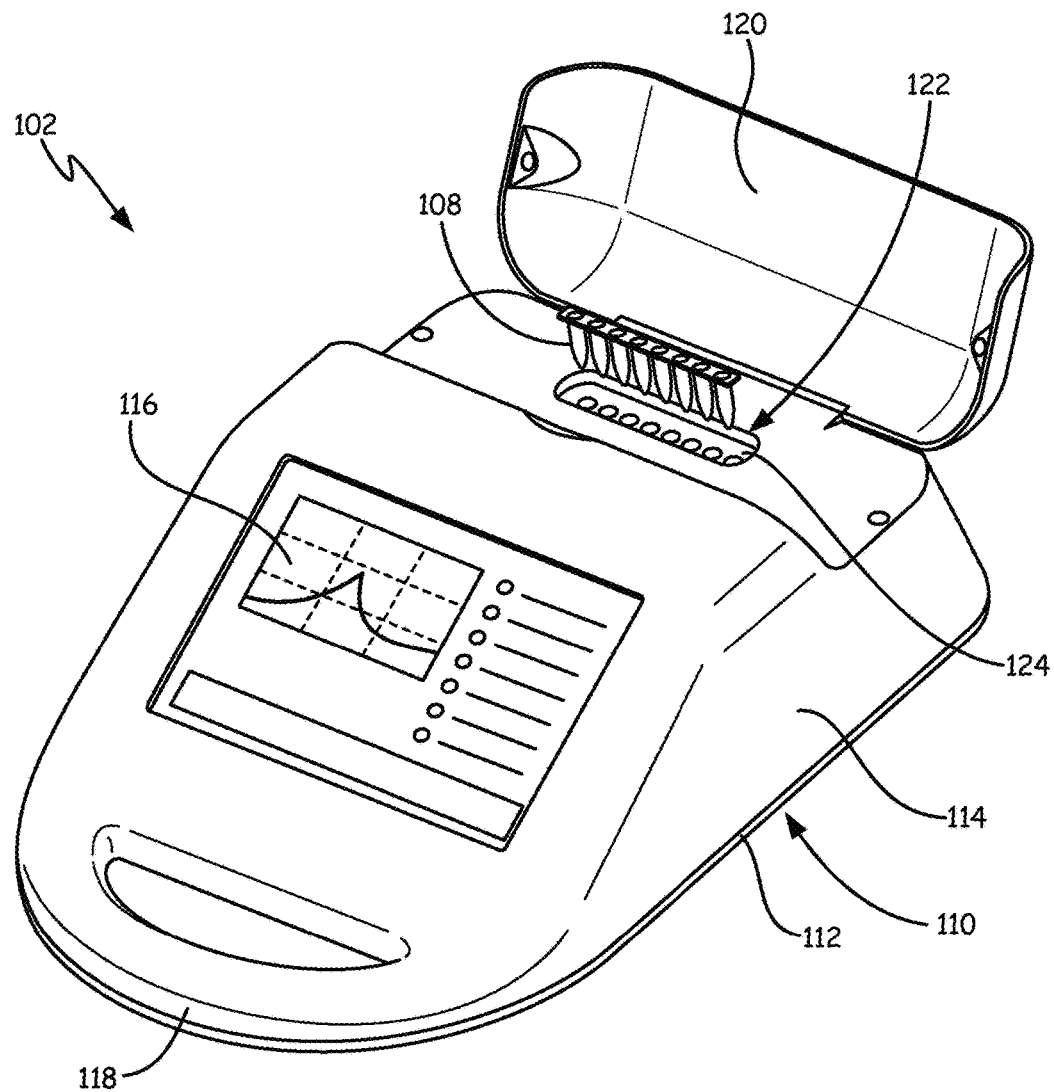
FIG. 2B is a perspective view of the base unit when a sample holder in the form of a tube array is being placed in the base unit.

FIG. 2A is a perspective view of base unit 102. FIG. 2B is a perspective view of base unit 102 when a sample holder in the form of tube array 108 is being placed in base unit 102. Base unit 102 includes housing 110 (including first housing portion 112 and second housing portion 114), display 116, handle 118, lid 120, receptacle 122 (shown in FIG. 2B), and optical assembly 124 (shown in FIG. 2B). FIG. 2B also shows tube array 108.

Base unit 102 is used to analyze biological samples that have been mixed with a reaction mixture (also referred to as a biological sample and reagent mixture). Housing 110 forms the body of base unit 102. Housing 110 includes first housing portion 112 and second housing portion 114. First housing portion 112 forms a base portion of base unit 102 and second housing portion 114 forms a top portion of base unit 102. Located on a front top side of housing 110 is display 116. Display 116 is a touchscreen display in the embodiment shown, but can be any suitable display in alternate embodiments. A user can use display 116 to select test protocol and set up the parameters for tests that will be run in base unit 102. A user can also use display 116 to provide sample and assay traceability information to base unit 102. Display 116 will also display data that is collected during testing.

Housing 110 further includes handle 118. Handle 118 is located on a front side of housing 110 in the embodiment shown, but can be located in any suitable location in alternate embodiments. Handle 118 is shown as an integrated handle with housing 110 in the embodiment shown, but can be attached to base unit 102 in any suitable manner in alternate embodiments. Handle 118 is included on base unit 102 so that base unit 102 can be easily transported in the field.

As seen in FIG. 2B, receptacle 122 is located on a top side of base unit 102 in the embodiment shown, but can be located in any suitable location in alternate embodiments. Receptacle 122 is an opening in housing 110 of base unit 102. A sample holder containing a biological sample and reagent mixture can be placed in receptacle 122 for testing. In FIG. 2B, receptacle 122 is configured to receive tube array 108. In alternate embodiments, receptacle 122 can be configured in any manner that is capable of receiving a sample holder.

Housing 110 also includes lid 120. Lid 120 is located on a top side of housing 110 in the embodiment shown, but can be located in any suitable location in alternate embodiments. Lid 120 is included on base unit 102 to cover receptacle 122. When a sample holder is placed in receptacle 122 of base unit 102 it will be positioned in optical assembly 124 that is held in base unit 102. Optical assembly 124 is positioned just below receptacle 122 and can be accessed through receptacle 122. Optical assembly 124 will be able to amplify, excite, and detect the biological sample in the sample holder. Optical assembly 124 includes a heating component that is used to heat the biological sample, causing it to amplify. The heating component can heat the biological sample at a constant temperature or the heating component can cycle the biological sample through different temperatures. Optical assembly 124 will then use radiation to excite the biological sample, so that the biological sample with emit radiation.

Lid 120 is positioned over receptacle 122 to prevent radiation from escaping housing 110 through receptacle 122. Lid 120 further prevents ambient light from entering housing 110 through receptacle 122, which prevents the ambient light from skewing or negating results of the tests that are being run in base unit 102. Lid 120 also covers receptacle 122 to prevent contamination from entering into receptacle 122 when base unit 102 is being used in the field. Lid 120 is capable of being moved between an open and closed position and can be held in the closed position with any suitable means. In the embodiment shown, lid 120 is held in a closed position with magnets. When lid 120 is in an open position, sample holders (including tube array 108) can be inserted into and removed from receptacle 122. When lid 120 is closed, sample holders will be held in receptacle 122 and radiation in base unit 102 will not escape from housing 110. When lid 120 is in a closed position, it puts pressure on the sample holder that is placed in a heat block in base unit 102. This improves engagement and heat transfer between the sample holder and the heat block in base unit 102.

Receptacle 122 can be shaped to receive any sample holder, allowing base unit 102 to be designed to accommodate a wide variety of standard and custom designed sample holders. Tube array 108 is a standard sample holder that is widely available on the market. A card can also be custom designed for use as a sample holder that is to be used with base unit 102. Receptacle 122 allows base unit 102 to be designed to accommodate a wide variety of sample holder shapes and sizes.

Base unit 102 is designed for use in the field and provides many advantages for such use. Biological materials that are collected in the field can be tested in the field as they are collected. This alleviates concerns about contamination or degradation of the biological sample, as there is no need to transport the biological sample back to a laboratory for testing. Further, base unit 102 allows a user to quickly react to results from tests that are run in the field. If a test is inconclusive, additional biological material can be collected and sampled right away. Further, if testing indicates that there is a pathogen or toxin in the sample, a user can initiate proper safety protocol right away to protect against the pathogen or toxin.

Base unit 102 includes a number of features that make it suitable for use in the field. Handle 118 is included to easily transport the device. Display 116 is integrated into base unit 102 so that base unit 102 can act as an all-in-one system, as base unit 102 is capable of testing a biological sample, processing the data that is collected, and displaying the data on display 116. Display 116 eliminates the need for base unit 102 to be connected to another machine or computer to process and display the results of testing. This can allow a user to avoid having to carry an additional device in the field or having to wait till they get back to a laboratory to read the data. Base unit 102 includes all of the features that are necessary for testing, processing, and displaying results of the tests in a compact all-in-one device.

Figure 3:
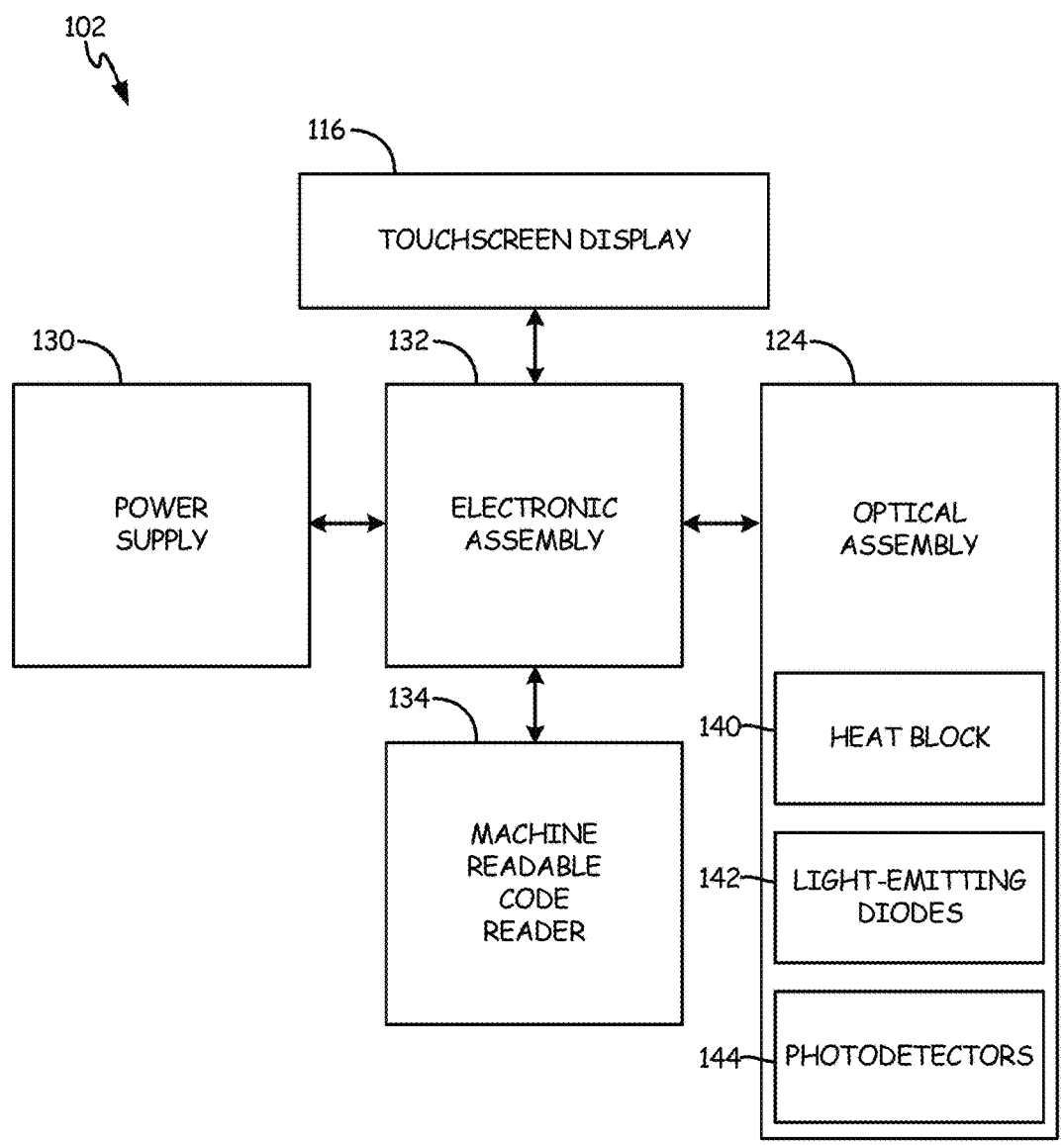
FIG. 3 is a block diagram of the base unit.

FIG. 3 is a block diagram of base unit 102. Base unit 102 includes display 116, power supply 130, electronic assembly 132, machine readable code reader 134, and optical assembly 124. Optical assembly 124 includes heat block 140, light-emitting diodes 142, and photodetectors 144.

Base unit 102 is used to analyze and obtain data from biological samples in the field. To accomplish this, base unit 102 is equipped with display 116, power supply 130, electronic assembly 132, machine readable code reader 134, and optical assembly 124. In the embodiment shown, display 116 is a touchscreen display that acts as a primary user interface between a user and base unit 102. A user can input information into display 116 to indicate what testing should be run in base unit 102 for each biological sample. Further, a user can monitor the results of tests that are run in base unit 102 on display 116.

Display 116 is connected to electronic assembly 132 with interface circuitry. Information that is inputted into display 116 will be communicated to electronic assembly 132 using the interface circuitry. Electronic assembly 132 includes hardware, firmware, and software to control the operations of base unit 102, including a microprocessor. Electronic assembly 132 will indicate what testing is to be run in base unit 102 and communicates this information throughout the device. Data that is collected in base unit 102 during testing will also be communicated to electronic assembly 132. Electronic assembly 132 can process this data and transmit it to display 116 to be displayed. Electronic assembly 132 further stores this data for retrieval or transfer at a later time.

Electronic assembly 132 is connected to power supply 130 with interface circuitry. Power supply 130 includes components that are capable of powering base unit 102, including a battery, a power board, a power switch, and a power jack that can be connected to a power source for recharging. Power from power supply 130 is sent to electronic assembly 132 through the interface circuitry so that base unit 102 can operate.

Base unit 102 can further include machine readable code reader 134. When a sample holder containing a machine readable code is placed in base unit 102, machine readable code reader 134 can read the machine readable code on the sample holder. A machine readable code can also be provided separate from the sample holder. The machine readable code can contain all of the parameters for the testing protocol and the assay traceability information for the test that is to be run. Alternatively, the machine readable code can indicate what test is to be run. This is advantageous, as it allows a user to insert a sample into base unit 102 and base unit 102 will automatically select a test protocol and begin testing.

Electronic assembly 132 includes a microprocessor, associated memory, and interface circuitry for interfacing with display 116 and optical assembly 124. Input that is received in electronic assembly 132 from display 116 can be processed in electronic assembly 132. This information can be used to control optical assembly 124. Optical assembly 124 conducts testing of the biological sample that is placed in base unit 102. As the testing is being completed, data that is collected in optical assembly 124 can be communicated to electronic assembly 132. Electronic assembly 132 processes this data and can transmit the data to display 116 so that the user can monitor the test results. Electronic assembly 132 can also transmit the data to an external device with any suitable data transfer means, including wireless transfer or transfer through a USB port, microUSB port, SD card, or microSD card.

Optical assembly 124 includes heat block 140, light-emitting diodes 142, and photodetectors 144 to conduct testing of the biological samples that are placed in base unit 102. Optical assembly 124 will amplify the biological sample using heat and will then excite the biological sample with radiation to detect the presence of a specific fluorescent marker. Biological samples that are placed in base unit 102 will be mixed with a reaction mixture that contains one or more fluorescent dyes. When the biological sample is placed in base unit 102, heat block 140 will amplify the biological sample with heat. Heat block 140 is positioned underneath receptacle 122 in base unit 102 so that when a sample holder containing a biological sample is placed in base unit 102, the sample holder will be positioned in heat block 140. As the biological sample is amplified it can be analyzed using light-emitting diodes 142 and photodetectors 144. Light-emitting diodes 142 transmit radiation to the biological sample to excite the biological sample. A plurality of light-emitting diodes 142 can be used in base unit 102 to excite the biological sample at a predetermined cycle rate. In the embodiment shown, the plurality of light-emitting diodes 142 cycle on and off at 1.54 kHz. In alternate embodiments, light-emitting diodes 142 can cycle at any predetermined cycle rate. When the biological sample is excited at the predetermined cycle rate, it will emit radiation at the same predetermined cycle rate and the corresponding wavelengths of the fluorescent dyes that were added to the biological sample. This radiation can be received by photodetectors 144. A plurality of photodetectors 144 can be used in base unit 102 to read the emitted radiation from the biological sample at different radiation wavelengths. The signals produced by photodetectors 144 can then be transmitted to electronic assembly 132 for processing and analysis, and displayed on display 116 as data collected during testing.

Base unit 102 is advantageous, as it is an all-in-one device. Base unit 102 includes optical assembly 124 to conduct testing of biological samples in the field. Base unit 102 further includes electronic assembly 132 and display 116 to specify what testing to run and to process and display data that is collected during testing. Base unit 102 further includes power supply 130, including a battery, so that base unit 102 can be used in the field. Base unit 102 includes every component that is necessary to conduct testing of a biological sample, and does so in a compact device that can be easily used in the field. Using base unit 102 in the field prevents concerns about contamination or degradation of biological samples and allows a user to quickly react to test results in the field.

Figure 4:
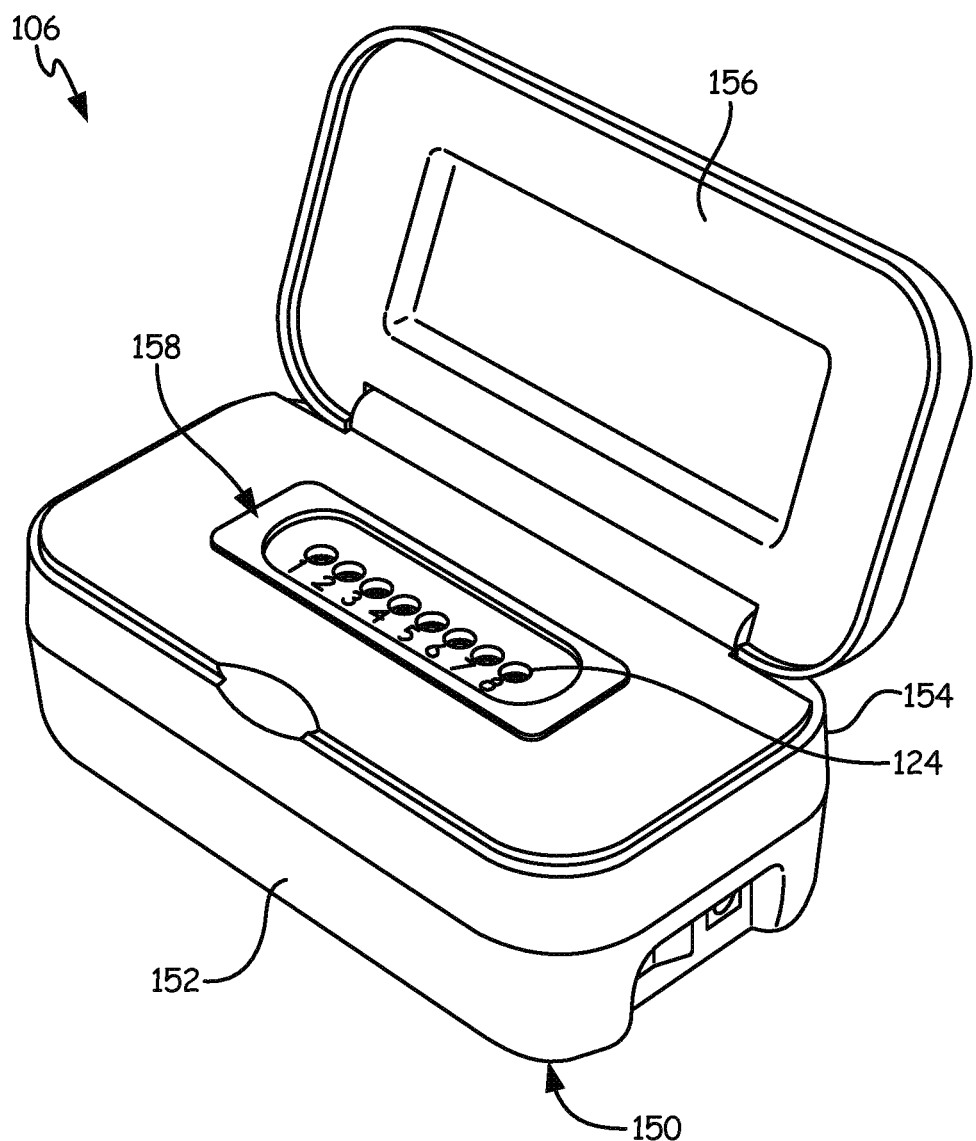
FIG. 4 is a perspective view of an expansion unit.

FIG. 4 is a perspective view of expansion unit 106. Expansion unit 106 includes housing 150 (including first housing portion 152 and second housing portion 154), lid 156, receptacle 158, and optical assembly 124.

Expansion unit 106 is used to analyze biological samples that have been mixed with a reaction mixture (also referred to as a biological sample and reagent mixture). Housing 150 forms the body of expansion unit 106. Housing 150 includes first housing portion 152 and second housing portion 154. First housing portion 152 forms a base portion of expansion unit 106 and second housing portion 154 forms a top portion of expansion unit 106. Expansion unit 106 further includes lid 156.

Receptacle 158 is located on a top side of expansion unit 106 in the embodiment shown, but can be located in any suitable location in alternate embodiments. Receptacle 158 is an opening in housing 150 of expansion unit 106. A sample holder containing a biological sample can be placed in receptacle 158 for testing. In the embodiment shown, receptacle 158 is configured to receive tube array 108 (not shown in FIG. 4). In alternate embodiments, receptacle 158 can be configured in any manner that is capable of receiving a sample holder.

Housing 150 also includes lid 156. Lid 156 is located on a top side of housing 150 in the embodiment shown, but can be located in any suitable location in alternate embodiments. Lid 150 is included on expansion unit 106 to cover receptacle 158. When a sample holder is placed in receptacle 158 of expansion unit 106 it will be positioned in optical assembly 124 that is held in expansion unit 106. Optical assembly 124 is positioned just below receptacle 158 and can be accessed through receptacle 158. Optical assembly 124 will be able to amplify, excite, and detect the biological sample in the sample holder. In the embodiment shown in FIG. 4, optical assembly 124 includes a heating component and detection components. The heating component is used to heat the biological sample, causing it to amplify. The heating component can heat the biological sample at a constant temperature or the heating component can cycle the biological sample through different temperatures. Optical assembly 124 will then use radiation to excite the biological sample, so that the biological sample with emit radiation which can then be detected by the detection components. In alternate embodiments, expansion unit 106 can include only a heating component or only detection components. Further, the heating component can heat the biological sample at a constant temperature, the heating component can cool the biological sample at a constant temperature, or the heating component can cycle the biological sample through a cycle of different temperatures.

Lid 156 is positioned over receptacle 158 to prevent radiation from escaping housing 150 through receptacle 158. Lid 156 further prevents ambient light from entering housing 150 through receptacle 158, which prevents the ambient light from skewing or negating results of the tests that are being run in expansion unit 106. Lid 156 also covers receptacle 158 to prevent contamination from entering into receptacle 158 when expansion unit 106 is being used in the field. Lid 156 is capable of being moved between an open and closed position and can be held in the closed position with any suitable means. When lid 156 is in an open position, sample holders (including tube array 108) can be inserted into and removed from receptacle 158. When lid 156 is closed, sample holders will be held in receptacle 158 and radiation in expansion unit 106 will not escape from housing 150. When lid 156 is in a closed position, it puts pressure on the sample holder that is placed in a heat block in expansion unit 106. This improves engagement and heat transfer between the sample holder and the heat block in expansion unit 106.

Receptacle 158 can be shaped to receive any sample holder, allowing expansion unit 106 to be designed to accommodate a wide variety of standard and custom designed sample holders. Tube array 108 is a standard sample holder that is widely available on the market. A card can also be custom designed for use as a sample holder that is to be used with expansion unit 106. Receptacle 158 allows expansion unit 106 to be designed to accommodate a wide variety of sample holder shapes and sizes.

Expansion unit 106 is advantageous, as it allows a user to increase the amount of tests the user is running in any given situation. Expansion unit 106 can be used in a laboratory setting or in the field. Expansion unit 106 can interface with a base unit, where the base unit indicates what testing the expansion unit 106 should conduct and when the testing should begin. Once data is collected in expansion unit 106, it can be communicated to the base unit. The data can be processed in expansion unit 106 before it is communicated to the base unit or it can be communicated to the base unit without being processed. The base unit can then run the test protocol to process the data.

Figure 5:
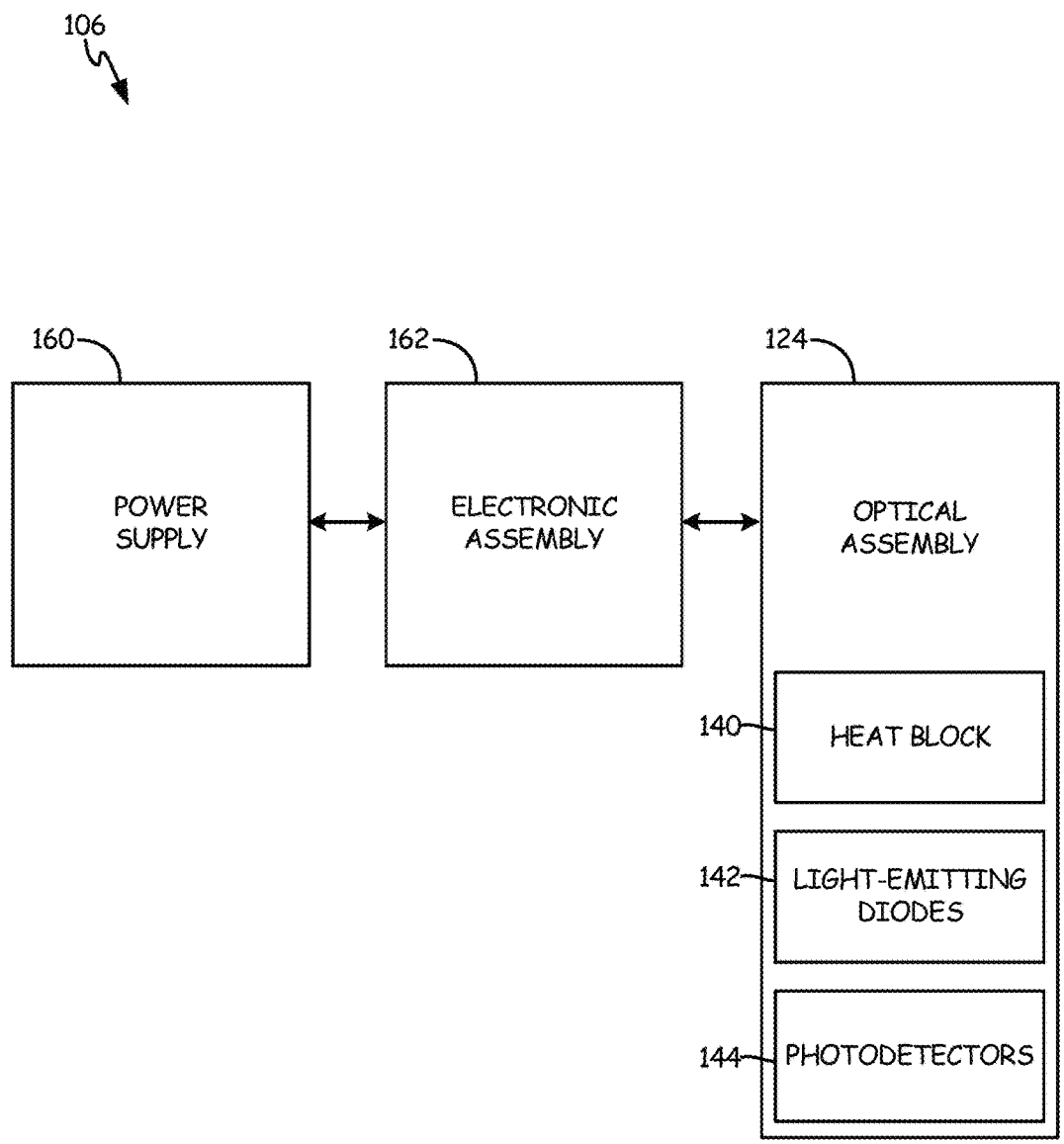
FIG. 5 is a block diagram of the expansion unit.

FIG. 5 is a block diagram of expansion unit 106. Expansion unit 106 includes power supply 160, electronic assembly 162, and optical assembly 124. Optical assembly 124 includes heat block 140, light-emitting diodes 142, and photodetectors 144.

Expansion unit 106 is used to analyze and obtain data from biological samples. To accomplish this, expansion unit 106 is equipped with power supply 160, electronic assembly 162, and optical assembly 124. Electronic assembly 162 includes hardware, firmware, and software to control the operations of expansion unit 106, including a microprocessor. Electronic assembly 162 also includes a communication interface that communicates with an electronic assembly in the base unit. The communication interface can be a hard wire interface or a wireless interface. The wireless interface can communicate via Bluetooth, Wi-Fi, Infrared, or any other wireless technology.

The electronic assembly in the base unit will indicate what testing is to be run in expansion unit 106 and will communicates this information to electronic assembly 162 in expansion unit 106. Data that is collected in expansion unit 106 during testing will be communicated to electronic assembly 162 in expansion unit 106. Electronic assembly 162 in expansion unit 106 will then communicate the data to the electronic assembly in the base unit. Data can be processed in expansion unit 106 before it is communicated to the base unit or it can be communicated to the base unit without being processed. The electronic assembly in the base unit can also process this data and transmit it to a display to be displayed. The electronic assembly in the base unit also stores this data for retrieval or transfer at a later time.

In one embodiment, expansion unit 106 could be docked to a base unit through hard wire interface circuitry. When expansion unit 106 is docked to the base unit, the base unit can provide instructions to expansion unit 106 through the hard wire interface circuitry. Expansion unit 106 can then be removed from the base unit and used to run tests. After testing is completed, expansion unit 106 can be docked to the base unit through the hard wire interface circuitry again to communicate the data collected during the testing to the base unit. In a second embodiment, expansion unit 106 can receive instructions from a base unit wirelessly by utilizing wireless interface circuitry. Expansion unit 106 can then be used to run tests. After testing is completed, expansion unit 106 can be docked to the base unit through hard wire interface circuitry to communicate the data collected during the testing to the base unit.

Electronic assembly 162 is connected to power supply 160 with interface circuitry. In the embodiment shown in FIG. 5, power supply 160 includes components that are capable of powering expansion unit 106, including a battery, a power board, a power switch, and a power jack that can be connected to a power source for recharging. Power from power supply 160 is sent to electronic assembly 162 through the interface circuitry so that expansion unit 106 can operate. In an alternate embodiment, expansion unit 106 can be powered by a base unit and power supply 160 will include a power jack that can be connected to the base unit to provide power to expansion unit 106.

Electronic assembly 162 further includes a microprocessor, associated memory, and interface circuitry for interfacing with optical assembly 124. Input that is received in electronic assembly 162 from the electronic assembly of the base unit can be processed in electronic assembly 162. This information can be used to control optical assembly 124. Optical assembly 124 conducts testing of the biological sample that is placed in expansion unit 106. As the testing is being completed, data that is collected in optical assembly 124 can be communicated to electronic assembly 162. Electronic assembly 162 processes this data and can transmit the data to the electronic assembly in the base unit. The electronic assembly in the base unit can then transmit the data to a display so that the user can monitor the test results. Electronic assembly 162 can also transmit the data to an external device with any suitable data transfer means, including wireless transfer or transfer through a USB port, microUSB port, SD card, or microSD card.

Optical assembly 124 includes heat block 140, light-emitting diodes 142, and photodetectors 144 to conduct testing of the biological samples that are placed in expansion unit 106. Optical assembly 124 will amplify the biological sample using heat and will then excite the biological sample with radiation to detect the presence of a specific fluorescent marker. Biological samples that are placed in expansion unit 106 will be mixed with a reaction mixture that contains one or more fluorescent dyes. When the biological sample is placed in expansion unit 106, heat block 140 will amplify the biological sample with heat. Heat block 140 is positioned underneath receptacle 158 in expansion unit 106 so that when a sample holder containing a biological sample is placed in expansion unit 106, the sample holder will be positioned in heat block 140. As the biological sample is amplified it can be analyzed using light-emitting diodes 142 and photodetectors 144. Light-emitting diodes 142 transmit radiation to the biological sample to excite the biological sample. A plurality of light-emitting diodes 142 can be used in expansion unit 106 to excite the biological sample at a predetermined cycle rate. In the embodiment shown, the plurality of light-emitting diodes 142 cycle on and off at 1.54 kHz. In alternate embodiments, light-emitting diodes 142 can cycle at any predetermined cycle rate. When the biological sample is excited at the predetermined cycle rate, it will emit radiation at the same predetermined cycle rate and the corresponding wavelengths of the fluorescent dyes that were added to the biological sample. This radiation can be received by photodetectors 144. A plurality of photodetectors 144 can be used in expansion unit 106 to read the emitted radiation from the biological sample at different radiation wavelengths. The signals produced by photodetectors 144 can then be transmitted to electronic assembly 162 for transmitting to the electronic assembly of the base unit. The electronic assembly of the base unit can then process and analyze the data, and display the data as the data is collected during testing.

Figure 6A:
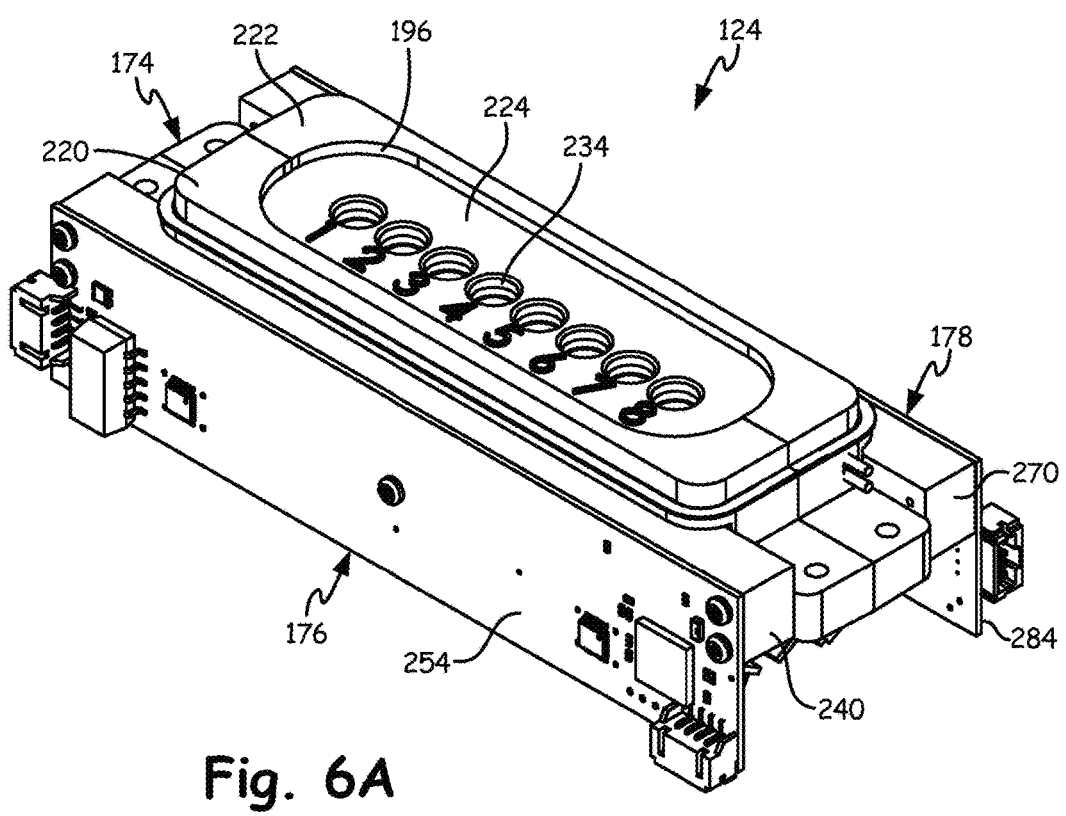
FIG. 6A is a perspective view of an optical assembly.
Figure 6B:
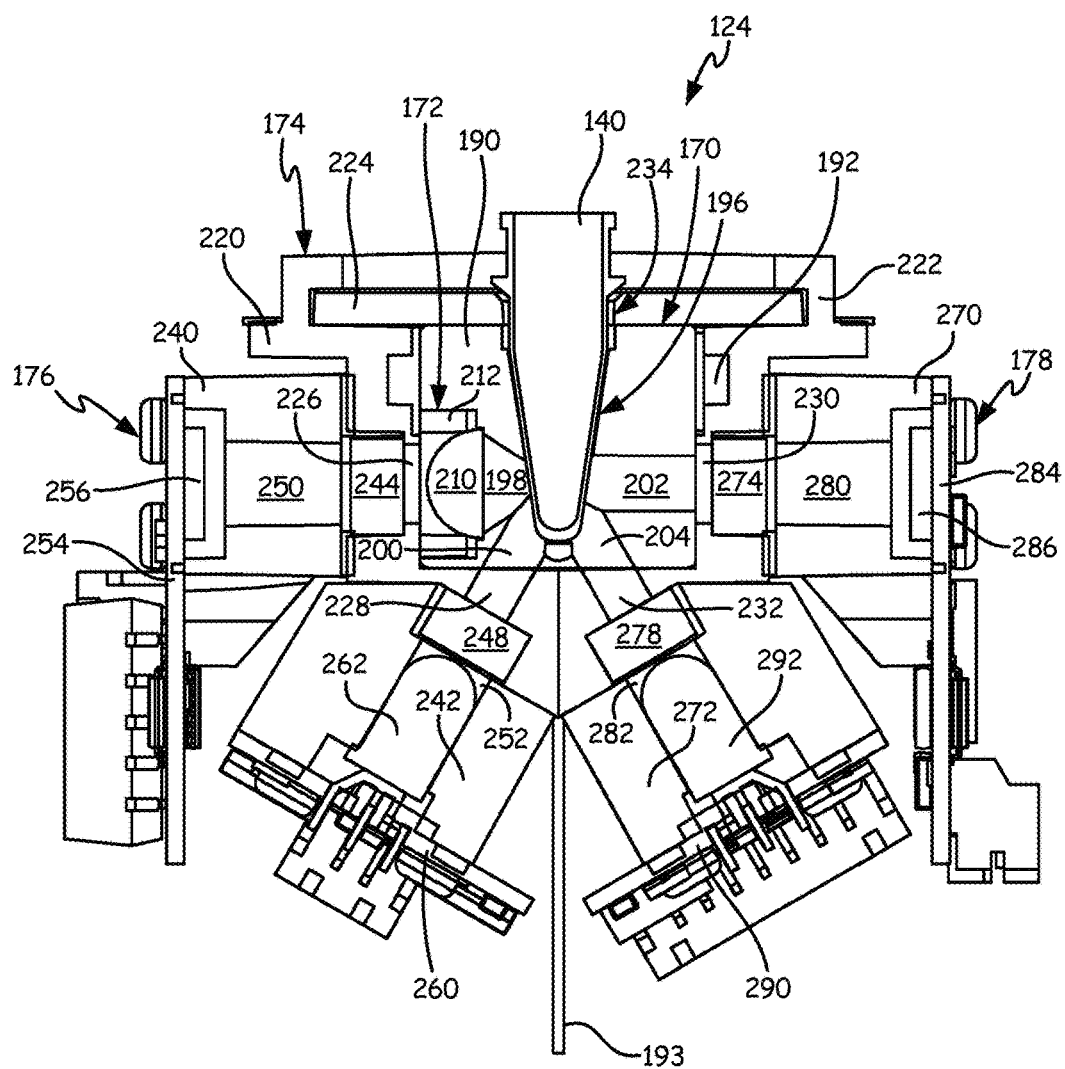
FIG. 6B is a cross-sectional view of the optical assembly.

FIG. 6A is a perspective view of optical assembly 124. FIG. 6B is a cross-sectional view of optical assembly 124. Optical assembly 124 includes heating portion 170 (not shown in FIG. 6A), lens portion 172 (not shown in FIG. 6A), housing portion 174, first optical mounting portion 176, and second optical mounting portion 178. Also shown in FIG. 6B is tube array 108.

Optical assembly 124 can be positioned in both base unit 102 and expansion units 106. Optical assembly 124 includes heating portion 170 to heat the biological sample and reagent mixture in tube array 108. Positioned in heating portion 170 is lens portion 172 to direct radiation through optical assembly 124. Housing portion 174 is positioned around heating portion 170 and forms the main body portion of optical assembly 124. First optical mounting portion 176 is positioned on a first side of housing portion 174 and second optical mounting portion 178 is positioned on a second side of housing portion 174. Both first optical mounting portion 176 and second optical mounting portion 178 mount light-emitting diodes to optical assembly 124 to excite the biological sample and reagent mixture in tube array 108. Further, both first optical mounting portion 176 and second optical mounting portion 178 mount photodetectors to optical assembly 124 to detect a signal from the biological sample and reagent mixture in tube array 108.

Figure 7:
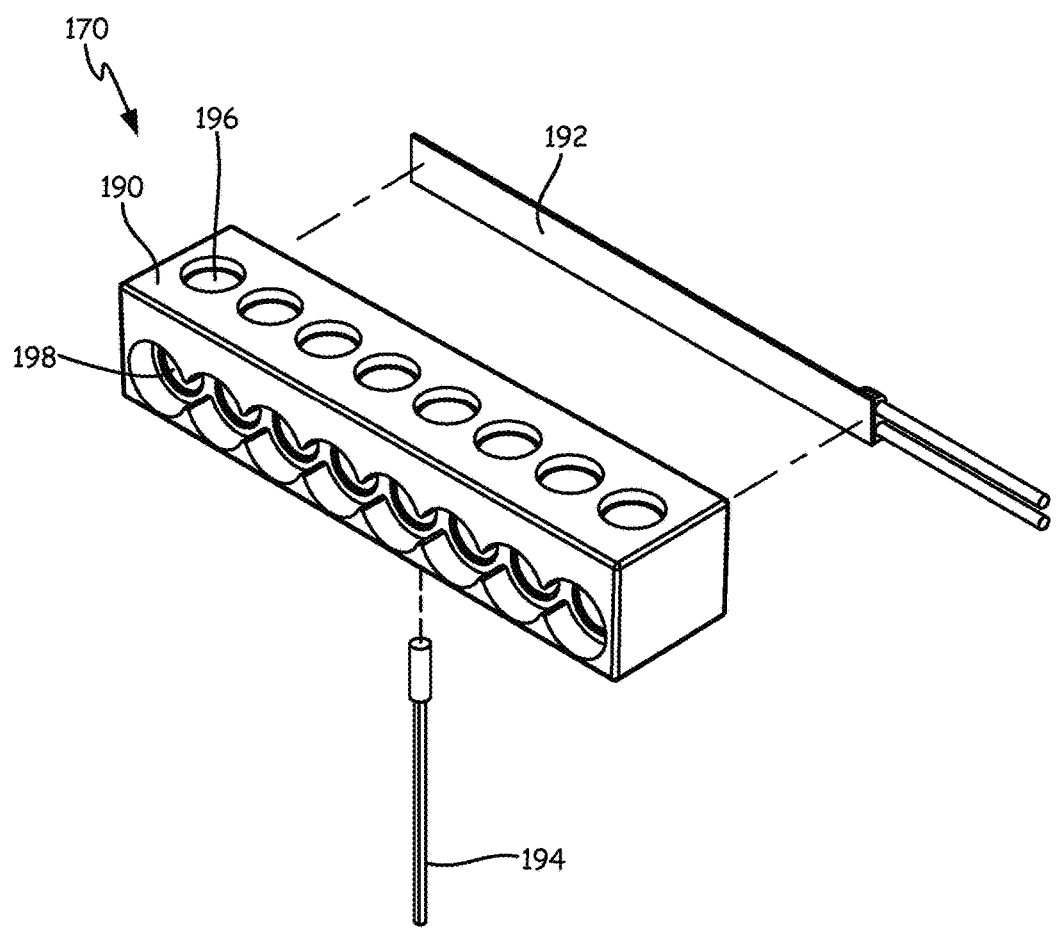
FIG. 7 is an exploded view of a heating portion of the optical assembly.

FIG. 7 is an exploded view of heating portion 170 of optical assembly 124. As seen in FIGS. 6B and 7, heating portion 170 includes sample block 190, heating component 192, temperature sensor 194, wells 196, passages 198, passages 200, passages 202, and passages 204.

Heating portion 170 includes sample block 190 that forms the main body portion of heating portion 170. Heating component 192 is attached to a second side of sample block 190. Heating component 192 is a flat polyimide heater in the embodiment shown, but can be any suitable heater in alternate embodiments. Temperature sensor 194 is placed in a bottom portion of sample block 190 to sense the temperature of sample block 190. Further, in alternate embodiments, a thermal cut out switch, such as a PEPI switch, can be placed in series with a lead on heating component 192.

Sample block 190 includes wells 196 on a top side of sample block 190. Each well 196 is sized to receive one tube in tube array 108. In the embodiment shown in FIG. 7, heating component 192 heats each of wells 196 at a constant temperature so that modular testing device 100 can be used with isothermal amplification chemistries. In alternate embodiments, heating component 192 can heat each well 196 at a different temperature across a gradient, or there can be a plurality of heating components so that each well is heated by a different heating component to a different temperature. This allows a user to conduct a preliminary test to determine what temperature should be used to analyze a particular biological sample. In further alternate embodiments, heating component 192 can include a thermal cycler that is capable of cycling heating portion 170 through different temperatures so that modular testing device 100 can be used with non-isothermal polymerase chain reaction (PCR) chemistries.

Sample block 190 further includes passages 198, passages 200, passages 202, and passages 204. Passages 198 extend from a first side of sample block 190 to wells 196. Passages 200 extending from a bottom side of sample block 190 to wells 196. Passages 202 extend from the second side of sample block 190 to wells 196. Passages 204 extend from a bottom side of sample block 190 to wells 196. Passages 198, passages 200, passages 202, and passages 204 extend through sample block 190 to direct radiation into and out of the biological sample and reagent mixture in tube array 108 in wells 196.

Figure 8:
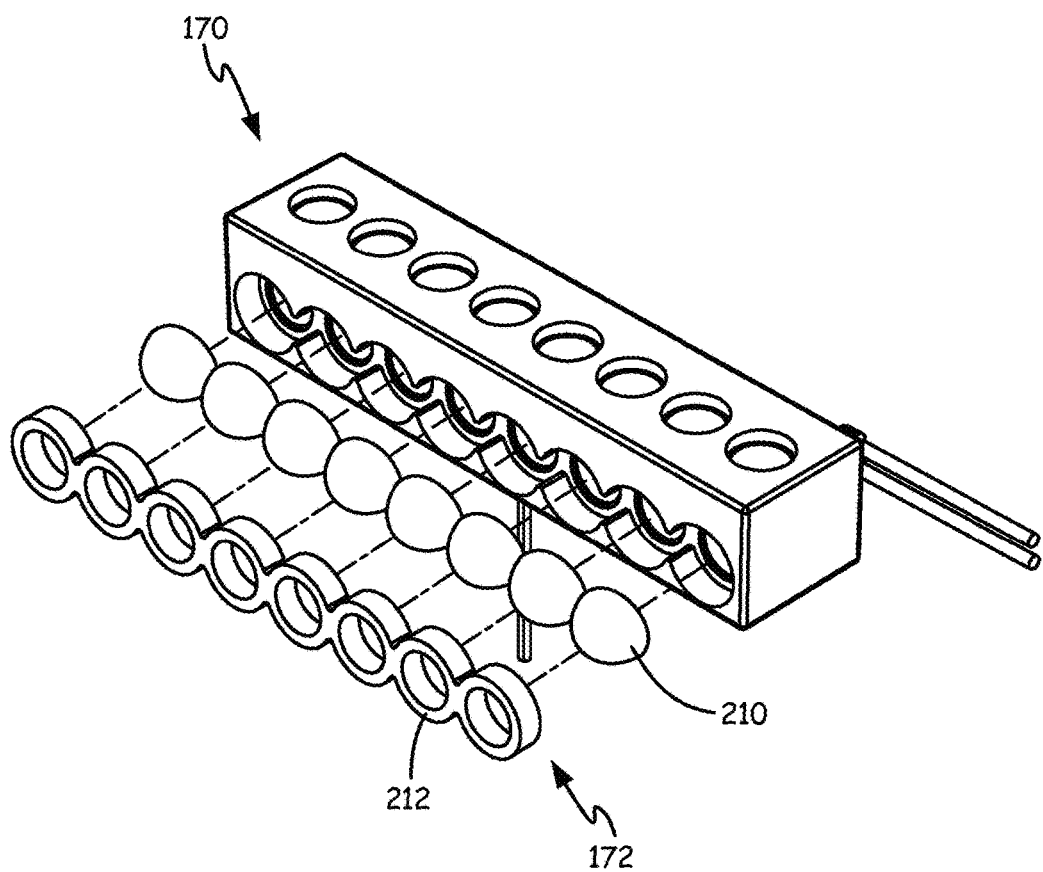
FIG. 8 is an exploded view of a lens portion of the optical assembly.

FIG. 8 is an exploded view of lens portion 172 of optical assembly 124. As seen in FIGS. 6B and 8, lens portion 172 includes lenses 210 and lens retainer 212.

Lens portion 172 includes lenses 210 that are positioned in sample block 190 of heating portion 170. Passages 198 in sample block 190 are sized to receive lenses 210 on the first side of sample block 190. One lens 210 is positioned in each passage 198 of sample block 190. Lenses 210 are held in passages 198 with lens retainer 212. Lens retainer 212 has a plurality of apertures so that radiation can pass through lens retainer 212 to pass through lenses 210.

Figure 9:
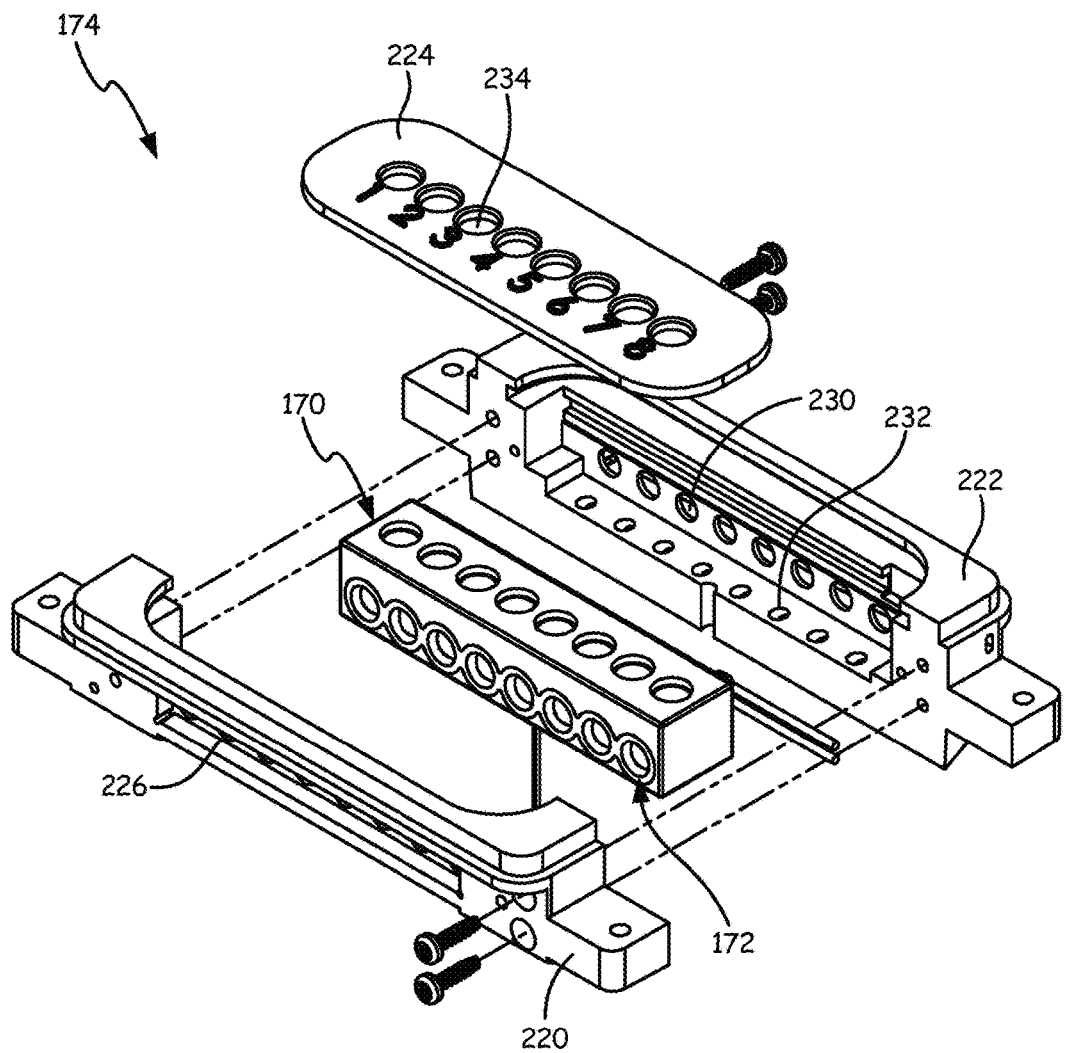
FIG. 9 is an exploded view of a housing portion of the optical assembly.

FIG. 9 is an exploded view of housing portion 174 of optical assembly 124. As seen in FIGS. 6A-6B and 9, housing portion 174 includes first housing 220, second housing 222, heat shield 224, passages 226, passages 228, passages 230, passages 232, and apertures 234.

Housing portion 174 includes first housing 220 positioned on a first side of heating portion 170 and second housing 222 positioned on a second side of heating portion 170. First housing 220 and second housing 222 form a main body portion of housing portion 174. Heat shield 224 is positioned between first housing 220 and second housing 222 on a top side of heating portion 170.

First housing 220 includes passages 226 and passages 228. Passages 226 extend from a first side of first housing 220 to an interior side of first housing 220 adjacent sample block 190. Each passage 226 in first housing 220 is aligned with one passage 198 in sample block 190. Passages 228 extend from a bottom side of first housing 220 to an interior side of first housing 220 adjacent sample block 190. Each passage 228 in first housing 220 is aligned with one passage 200 in sample block 190. Passages 226 and 228 extend through first housing 220 to direct radiation into and out of the biological sample and reagent mixture in tube array 108 in wells 196 of sample block 190.

Second housing 222 includes passages 230 and passages 232. Passages 230 extend from a second side of second housing 222 to an interior side of second housing 222 adjacent sample block 190. Each passage 230 in second housing 222 is aligned with one passage 202 in sample block 190. Passages 232 extend from a bottom side of second housing 222 to an interior side of second housing 222 adjacent sample block 190. Each passage 232 in second housing 222 is aligned with one passage 204 in sample block 190. Passages 230 and 232 extend through second housing 222 to direct radiation into and out of the biological sample and reagent mixture in tube array 108 in wells 196 of sample block 190.

Heat shield 224 is positioned over sample block 190 and held between first housing 220 and second housing 222. Apertures 234 extend from a top side to a bottom side of heat shield 224. Each aperture 234 in heat shield 224 is aligned with one well 196 in sample block 190. This allows tube array 108 to be positioned in wells 196 in sample block 190 through apertures 234 in heat shield 224. Heat shield 224 is positioned over sample block 190 to prevent heat from escaping out of the top side of sample block 190. Heat shield 224 further provides an insulated surface to protect the user from the top side of sample block 190 when sample block 190 is hot.

Figure 10A:
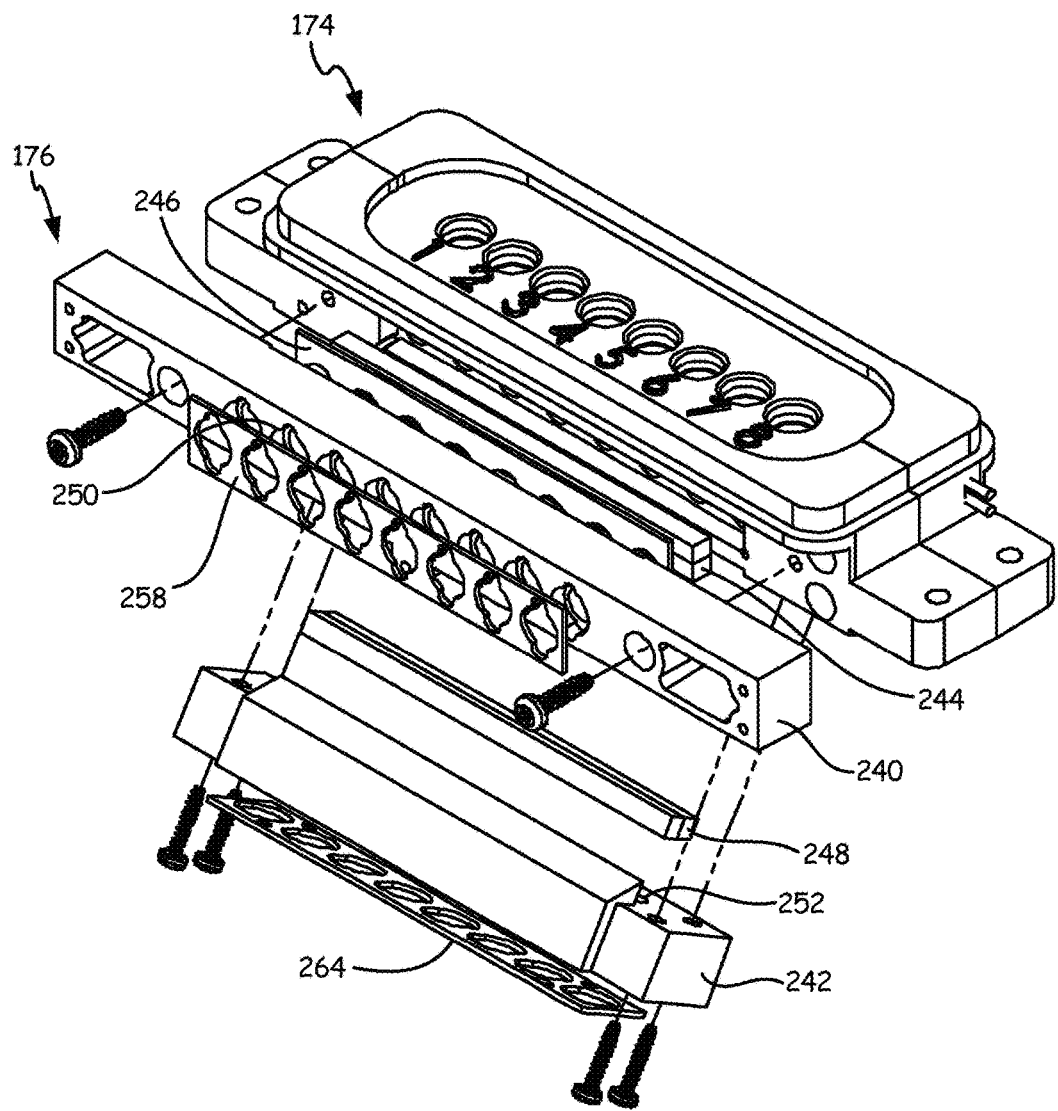
FIG. 10A is a partially exploded view of a first optical mounting portion of the optical assembly.
Figure 10B:
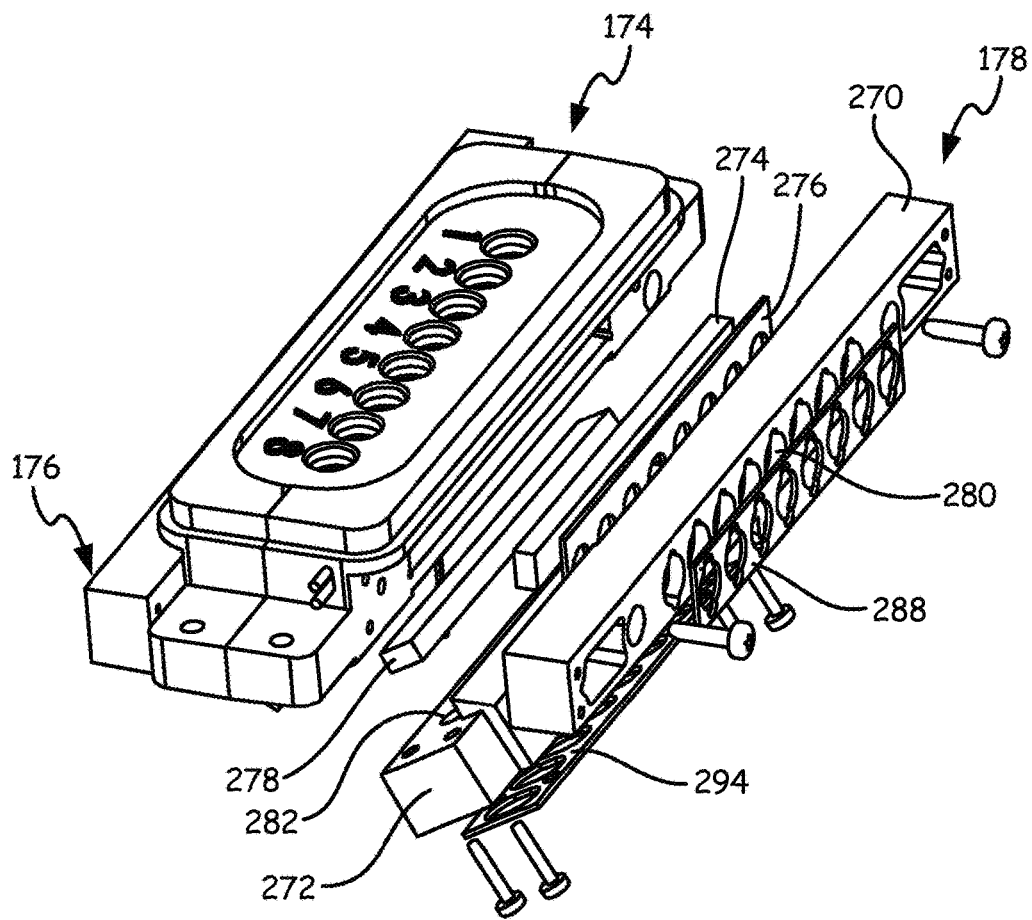
FIG. 10B is a partially exploded view of a second optical mounting portion of the optical assembly.
Figure 10C:
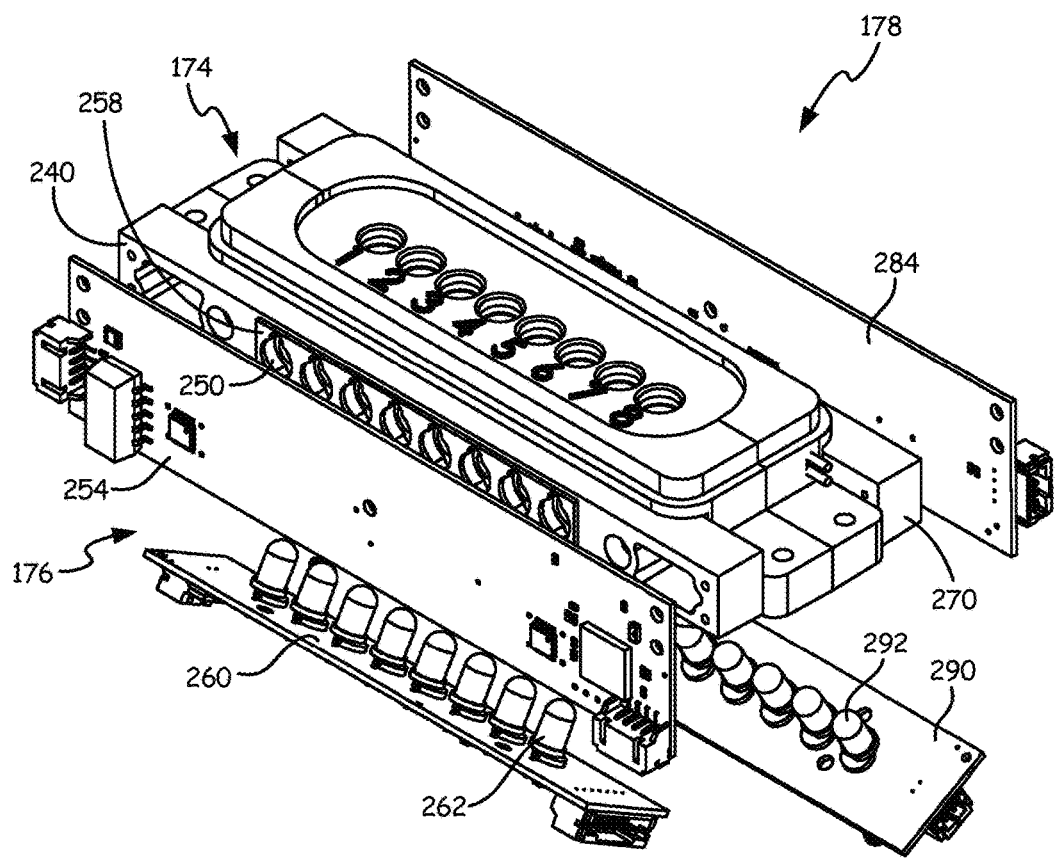
FIG. 10C is a partially exploded view of the first optical mounting portion and the second optical mounting portion of the optical assembly.

FIG. 10A is a partially exploded view of first optical mounting portion 176 of optical assembly 124. FIG. 10B is a partially exploded view of second optical mounting portion 178 of optical assembly 124. FIG. 10C is a partially exploded view of first optical mounting portion 176 and second optical mounting portion 178 of optical assembly 124. As seen in FIGS. 6A-6B, 10A, and 10C, first optical mounting portion 176 includes housing 240, housing 242, emission filter 244, gasket 246, excitation filter 248, passages 250, passages 252, photodetectors mounting board 254, photodetectors 256, gasket 258, light-emitting diodes mounting board 260, light-emitting diodes 262, and gasket 264. As seen in FIGS. 6A-6B and 10B-10C, second optical mounting portion 178 includes housing 270, housing 272, emission filter 274, gasket 276, excitation filter 278, passages 280, passages 282, photodetectors mounting board 284, photodetectors 286, gasket 288, light-emitting diodes mounting board 290, light-emitting diodes 292, and gasket 294.

First optical mounting portion 176 is positioned on a first side of housing portion 174. First optical mounting portion 176 includes housing 240 and housing 242 that form a main body portion of first optical mounting portion 176. Housing 240 is attached to a first side of first housing 220 of housing portion 174. Emission filter 244 is positioned between housing 240 and first housing 220 in a groove on the first side of first housing 220. Gasket 246 is positioned between emission filter 244 and housing 240. Housing 242 is attached to a bottom side of first housing 220 of housing portion 174. Excitation filter 248 is positioned between housing 242 and first housing 220 in a groove on the bottom side of first housing 220.

Housing 240 includes passages 250. Passages 250 extend from a first side of housing 240 to an interior side of housing 240 adjacent first housing 220. Each passage 250 in housing 240 is aligned with one passage 226 in first housing 220. Housing 242 includes passages 252. Passages 252 extend from a bottom side of housing 252 to an interior side of housing 242 adjacent first housing 220. Each passage 252 in housing 242 is aligned with one passage 228 in first housing 220.

Photodetectors mounting board 254 is connected to a first side of housing 240. Photodetectors mounting board 254 is an electronic board that includes photodetectors 256. Each photodetector 256 on photodetectors mounting board 254 is positioned in one passage 250 in housing 240. Gasket 258 is positioned between photodetectors mounting board 254 and housing 240. Light-emitting diodes mounting board 260 is attached to a bottom side of housing 242. Light-emitting diodes mounting board 260 is an electronic board that includes light-emitting diodes 262. Each light-emitting diode 262 on light-emitting diodes mounting board 260 is positioned in one passage 252 in housing 242. Gasket 264 is positioned between light-emitting diodes mounting board 260 and housing 242.

Second optical mounting portion 178 is positioned on a second side of housing portion 174. Second optical mounting portion 178 includes housing 270 and housing 272 that form a main body portion of second optical mounting portion 178. Housing 270 is attached to a second side of second housing 222 of housing portion 174. Emission filter 274 is positioned between housing 270 and second housing 222 in a groove on the second side of second housing 222. Gasket 276 is positioned between emission filter 274 and housing 270. Housing 272 is attached to a bottom side of second housing 222 of housing portion 174. Excitation filter 278 is positioned between housing 272 and second housing 222 in a groove on the bottom side of second housing 222.

Housing 270 includes passages 280. Passages 280 extend from a second side of housing 270 to an interior side of housing 270 adjacent second housing 222. Each passage 280 in housing 270 is aligned with one passage 230 in second housing 222. Housing 272 includes passages 282. Passages 282 extend from a bottom side of housing 282 to an interior side of housing 282 adjacent second housing 222. Each passage 282 in housing 272 is aligned with one passage 232 in second housing 222.

Photodetectors mounting board 284 is connected to a first side of housing 270. Photodetectors mounting board 284 is an electronic board that includes photodetectors 286. Each photodetector 286 on photodetectors mounting board 284 is positioned in one passage 280 in housing 270. Gasket 288 is positioned between photodetectors mounting board 284 and housing 270. Light-emitting diodes mounting board 290 is attached to a bottom side of housing 272. Light-emitting diodes mounting board 290 is an electronic board that includes light-emitting diodes 292. Each light-emitting diode 292 on light-emitting diodes mounting board 290 is positioned in one passage 282 in housing 272. Gasket 294 is positioned between light-emitting diodes mounting board 290 and housing 272.

As seen in FIGS. 6A-10C, optical assembly 124 can excite and detect emissions from a biological sample and reagent mixture in tube array 108 that is positioned in optical assembly 124. Light-emitting diodes 262 are bi-color light-emitting diodes that can emit radiation at two different wavelengths. In the embodiment shown, light-emitting diodes 262 are blue and amber bi-color light-emitting diodes to excite Fluorescein amidite (FAM) fluorescence dye and 6-Carboxyl-X-Rhodamine (ROX) fluorescence dye, respectively. Further, light-emitting diodes 262 emit radiation at a predetermine cycle rate of 1.54 kHz. Radiation from light-emitting diodes 262 can pass through passages 252, excitation filter 248, passages 228, and passages 200 into the biological sample and reagent mixture in tube array 108 that is held in wells 196. Excitation filter 248 is a dual bandpass excitation filter that is capable of passing either of the wavelengths emitted by light-emitting diodes 262. Excitation filter 248 is a single filter that extends across the entire length of tube array 108, thus excitation filter 248 extends between adjacent passages 228 in first housing 220. Radiation from light-emitting diodes 262 can excite a fluorescent dye in the biological sample and reagent mixture. This excitation of the fluorescent dye will emit a signal from the biological sample and reagent mixture and the emission can pass through passages 198, passages 226, emission filter 244, and passages 250 to be detected by photodetectors 256. Emission filter 244 is a dual bandpass emission filter in the embodiment shown. Emission filter 244 is a single filter that extends across the entire length of tube array 108, thus emission filter 244 extends between adjacent passages 226 in first housing 220.

Light-emitting diodes 292 are light-emitting diodes that can emit radiation at a single wavelength spectrum. In the embodiment shown, light-emitting diodes 292 are green light-emitting diodes to excite 6-carboxy-X-hexachlorofluorescein (HEX) fluorescence dye. Further, light-emitting diodes 292 emit radiation at a predetermine cycle rate of 1.54 kHz. Radiation from light-emitting diodes 292 can pass through passages 282, excitation filter 278, passages 232, and passages 204 into the biological sample and reagent mixture in tube array 108 that is held in wells 196. Excitation filter 278 is a single bandpass filter that is capable of passing the wavelength emitted by light-emitting diodes 292. Excitation filter 278 is a single filter that extends across the entire length of tube array 108, thus excitation filter 278 extends between adjacent passages 232 in second housing 222. Radiation from light-emitting diodes 292 can excite a fluorescent dye in the biological sample and reagent mixture. This excitation of the fluorescent dye will emit a signal from the biological sample and reagent mixture and the emission can pass through passages 202, passages 230, emission filter 274, and passages 280 to be detected by photodetectors 286. Emission filter 274 is a single bandpass filter in the embodiment shown. Emission filter 274 is a single filter that extends across the entire length of tube array 108, thus emission filter 274 extends between adjacent passages 230 in second housing 222.

In an alternate embodiment, light-emitting diodes 292 can be bi-color light-emitting diodes that can emit radiation at two different wavelengths. Further, excitation filter 278 can be a dual bandpass filter that is capable of passing both of the wavelengths emitted by light-emitting diodes 292, and emission filter 274 can also be a dual bandpass filter. This would result in modular testing device 100 being capable of testing four different fluorescent dyes that can be mixed in with the biological sample and reagent mixture.

Light-emitting diodes 262 and light-emitting diodes 292 emit radiation in the form of light that is cycled at a predetermined rate of 1.54 kHz. This causes emissions from the biological sample and reagent mixture at the same predetermined rate. Photodetectors 256 and photodetectors 286 thus receive the emissions from the biological sample and reagent mixture at a rate of 1.54 kHz as well. The electronic circuitry connected to photodetectors 256 and photodetectors 286 is designed to electronically filter out all other frequencies except for 1.54 kHz. This will negate any ambient light or other radiation sources in modular testing device 100 that may interfere with the accuracy of the testing.

Having a single filter for emission filter 244, excitation filter 248, emission filter 274, and excitation filter 278 simplifies the design of modular testing device 100. This simplified design makes modular testing device 100 more suitable for use in the field. If one of emission filter 244, excitation filter 248, emission filter 274, or excitation filter 278 had to be replaced, it would be easy to replace the entire filter instead of a number of different individual filters. Further, using one filter for each of emission filter 244, excitation filter 248, emission filter 274, or excitation filter 278 reduces the cost of modular testing device 100.

Figure 11:
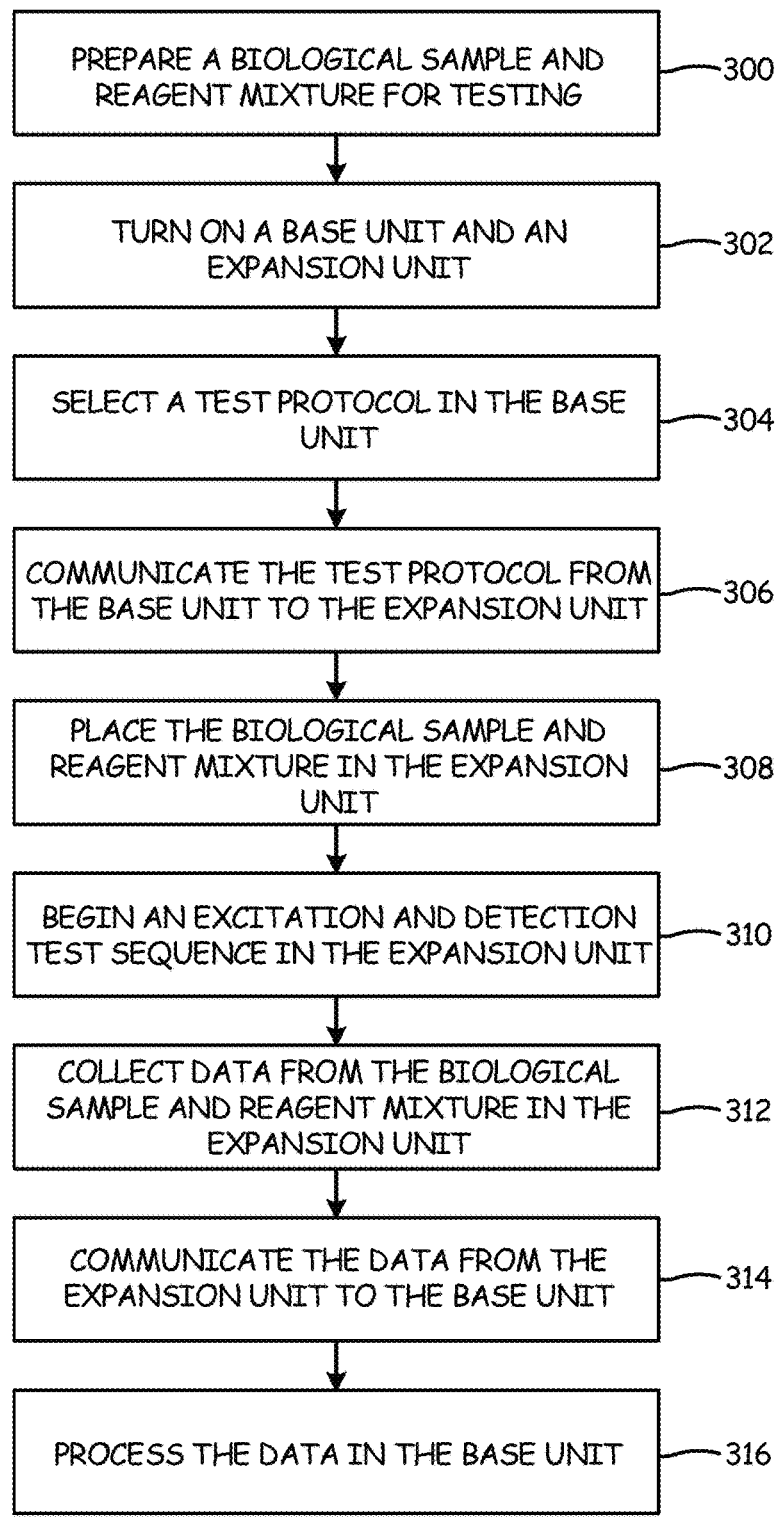
FIG. 11 is a flowchart showing steps for operating the modular testing device.

FIG. 11 is a flowchart showing steps for operating modular testing device 100. The flowchart includes steps 300-316.

Step 300 includes preparing a biological sample and reagent mixture for testing. The reagent mixture can contain the master mix necessary for the desired assay, including fluorescent dyes or markers such as FAM or ROX, necessary for detecting the desired analyte in modular testing device 100. Once a user acquires a biological sample, the biological sample can then be mixed with a reagent to form a biological sample and reagent mixture. More specifically, the biological sample is first mixed with a reaction buffer. Next, a portion of the biological sample and reaction buffer mixture is transferred to a sample holder containing a dried down master mix. This forms the biological sample and reagent mixture for testing. The biological sample and reaction mixture can be tested in the sample holder containing the dried down master mix or transferred to a different sample holder for testing.

In step 302, both the base unit and expansion unit 106 are turned on. In step 304, a test protocol is selected in the base unit. This can be done by scanning a code with machine readable code reader 154. The code will contain information about what test protocol is to be run and what parameters should be used. The test protocol can also be selected on the display of the base unit and the parameters can be inputted into the base unit. Step 306 includes communicating the selected test protocol from the base unit to expansion unit 106. Expansion unit 106 can then begin heating to the required temperature for the selected test protocol. When expansion unit 106 is preheated, it can communicate with the base unit. The base unit will visually and audibly notify the user that expansion unit 106 is ready for testing. In step 308, the user opens lid 156 of expansion unit 106 and places the sample holder with the biological sample and reagent mixture into heating assembly 170 in expansion unit 106.

In step 310, the user begins the excitation and detection sequence for the desired assay using the user interface on the display of the base unit. The base unit then communicates with expansion unit 106 to indicated to expansion unit 106 that testing can begin. Optical assembly 124 in expansion unit 106 then begins the excitation and detection sequence. Step 312 includes collecting data from the biologicals sample and reagent mixture in expansion unit 106 during the excitation and detection sequence. Step 314 includes communicating the data from expansion unit 106 to the base unit. Data is transmitted from optical assembly 124 to electronic assembly 162 in expansion unit 106. The data can be processed by electronic assembly 162 in expansion unit 106 before being communicated to the base unit. Electronic assembly 162 in expansion unit 106 then communicates the data to an electronic assembly in the base unit. Step 316 includes processing the data in the base unit. The processed data can then be displayed in the base unit to the user.

Steps 312, 314, and 316 can be done in real-time as data is being collected form the biological sample and reagent mixture in expansion unit 106. The electronic assembly and the display in the base unit can also log the data received from expansion unit 106 and monitor the data for threshold activity. Once the assay is complete, the display signals a positive, negative, or indeterminate outcome to the user. The electronic assembly of the base unit can also store the data obtained for retrieval or transfer.

Steps 300-316 described above apply to both base unit 102 and base unit 104. If base unit 102 is used, additional testing can be conducted in base unit 102 at the same time as testing is being conducted in expansion unit 106. Base unit 102 can be preheated at the same time as expansion unit 106, and lid 120 of base unit 102 can be opened so that a sample holder containing a biological sample and reagent mixture can be placed in heating assembly 10 of base unit 102. Further, base unit 102 can begin the excitation and detection sequence for the desired assay at the same time as expansion unit 106 and data can be collected biological sample and reagent mixture in base unit 102. Base unit 102 can display the data collected in base unit 102 and expansion unit 106 on display 116.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A modular testing device comprising:
a base unit; and
an expansion unit that communicates with the base unit, wherein the expansion unit comprises:
a housing;
a receptacle in which a sample holder containing a biological sample and reagent mixture can be placed; and
an optical assembly positioned in the housing, wherein the optical assembly is configured to amplify and detect a signal from the biological sample and reagent mixture, wherein data that is collected in the optical assembly is communicated to the base unit, and wherein the optical assembly of the expansion unit includes an excitation filter that extends across the entire optical assembly and an emission filter that extends across the entire optical assembly.

2. The modular testing device of claim 1, wherein the expansion unit communicates with the base unit over a hard wire connection.

3. The modular testing device of claim 1, wherein the expansion unit communicates with the base unit over a wireless connection.

4. The modular testing device of claim 1, wherein the modular testing device includes a plurality of expansion units that each communicate directly with the base unit.

5. The modular testing device of claim 1, wherein the modular testing device includes a plurality of expansion units, wherein a first expansion unit communicates directly with the base unit and the other expansion units communicate with the base unit through the first expansion unit.

6. The modular testing device of claim 1, wherein the base unit comprises:
a housing with an integrated touchscreen display;
a receptacle in which a sample holder containing a biological sample and reagent mixture can be placed; and
an optical assembly positioned in the housing, wherein the optical assembly is configured to amplify and detect a signal from the biological sample and reagent mixture; and
an electronic assembly that is configured to receive data from the optical assembly and transmit it for display on the touchscreen display; and
a power supply in the housing to power the base unit.

7. The modular testing device of claim 6, wherein the optical assembly of the base unit includes an excitation filter that extends across the entire optical assembly and an emission filter that extends across the entire optical assembly.

8. The modular testing device of claim 1, wherein the base unit is a computer selected from the group consisting of a desktop computer, a laptop computer, a tablet computer, a mobile phone, a smart watch, and an embedded PC.

9. The modular testing device of claim 1, wherein the expansion unit further comprises:
an electronic assembly that is configured to receive data from the optical assembly and transmit it to the base unit; and
a power supply in the housing to power the expansion unit.

10. A modular testing device comprising:
a base unit that comprises:
a housing with an integrated touchscreen display;
a receptacle in which a sample holder containing a biological sample and reagent mixture can be placed; and
an optical assembly positioned in the housing, wherein the optical assembly is configured to amplify and detect a signal from the biological sample and reagent mixture; and
an expansion unit that communicates with the base unit, wherein the expansion unit comprises:
a housing;
a receptacle in which a sample holder containing a biological sample and reagent mixture can be placed; and
an optical assembly positioned in the housing, wherein the optical assembly is configured to amplify and detect a signal from the biological sample and reagent mixture, and wherein the optical assembly in the expansion unit comprises:
a heating component to heat the biological sample and reagent mixture in the sample holder;
a plurality of light-emitting diodes configured to excite the biological sample and reagent mixture in the sample holder, wherein the plurality of light-emitting diodes are positioned on a first side of an excitation filter that extends across the entire optical assembly and the sample holder is positioned on a second side of the excitation filter; and
a plurality of photodetectors configured to detect a signal from the biological sample and reagent mixture in the sample holder, wherein the plurality of photodetectors are positioned on a first side of an emission filter that extends across the entire optical assembly and the sample holder is positioned on a second side of the emission filter.

11. The modular testing device of claim 10, wherein the base unit further comprises:
an integrated handle to allow for transport of the base unit;
a lid over the receptacle that is movable between an open and closed position;
an electronic assembly that is configured to receive data from the optical assembly and transmit it for display on the touchscreen display, and that is configured to receive data from the expansion unit and transmit it for display on the touchscreen display;
a power supply in the housing to power the base unit; and
a machine readable code reader in the housing for reading a machine readable code.

12. The portable testing device of claim 10, wherein the optical assembly in the base unit comprises:
a heating component to heat the biological sample and reagent mixture in the sample holder;
a plurality of light-emitting diodes to excite the biological sample and reagent mixture in the sample holder, wherein the plurality of light-emitting diodes are positioned on a first side of an excitation filter that extends across the entire optical assembly and the sample holder is positioned on a second side of the excitation filter; and
a plurality of photodetectors to detect a signal from the biological sample and reagent mixture in the sample holder, wherein the plurality of photodetectors are positioned on a first side of an emission filter that extends across the entire optical assembly and the sample holder is positioned on a second side of the emission filter.

13. The modular testing device of claim 10, wherein the expansion unit further comprises:
an electronic assembly that is configured to receive data from the optical assembly and transmit it to the base unit; and
a power supply in the housing to power the expansion unit.

14. A method of analyzing a biological sample and reagent mixture in a modular testing device, the method comprising:
preparing a biological sample and reagent mixture for testing and placing the biological sample and reagent mixture in a sample holder;
placing the sample holder in a receptacle in an expansion unit, wherein the expansion unit comprises an optical assembly comprising an excitation filter that extends across the entire optical assembly and an emission filter that extends across the entire optical assembly;
beginning an excitation and detection test sequence with the optical assembly to analyze the biological sample and reagent mixture in the expansion unit;
collecting data from the biological sample and reagent mixture in the expansion unit, wherein the data that is collected is collected by the optical assembly; and
communicating the data from the expansion unit to a base unit.

15. The method of claim 14, wherein communicating the data from the expansion unit to the base unit includes communicating the data over a hard wired connection between the expansion unit and the base unit.

16. The method of claim 14, wherein communicating the data from the expansion unit to the base unit includes communicating the data over a wireless connection between the expansion unit and the base unit.

17. The method of claim 14, and further comprising:
processing the data in the expansion unit;
processing the data in the base unit; and
displaying the data on a screen of the base unit.

18. The method of claim 14, and further comprising:
turning on the base unit and the expansion unit;
selecting the test protocol in the base unit;
communicating the selected test protocol from the base unit to the expansion unit; and
pre-heating the expansion unit in accordance with the selected test protocol.

* * * * *